(12) United States Patent
Schaffer et al.

(10) Patent No.: US 7,906,705 B2
(45) Date of Patent: Mar. 15, 2011

(54) POLYNUCLEOTIDES AND POLYPEPTIDES ENCODED THEREFROM AND METHODS OF USING SAME FOR INCREASING BIOMASS IN PLANTS AND PLANTS GENERATED THEREBY

(75) Inventors: Arthur A. Schaffer, Hashmonaim (IL); Nir Dai, Givat Brenner (IL); Marina Petreikov, Rishon-LeZion (IL)

(73) Assignee: The State of Israel, Ministry of Agriculture & Rural Development, Agricultural Research Organization, (A.R.O.), Volcani Center, Beit-Dagan (IL)

( * ) Notice: Subject to any disclaimer, the term of this patent is extended or adjusted under 35 U.S.C. 154(b) by 543 days.

(21) Appl. No.: 11/822,256

(22) Filed: Jul. 3, 2007

(65) Prior Publication Data

US 2008/0010704 A1 Jan. 10, 2008

Related U.S. Application Data

(60) Provisional application No. 60/817,687, filed on Jul. 3, 2006.

(51) Int. Cl.
*C12N 15/82* (2006.01)
*C12N 15/00* (2006.01)
*A01H 1/00* (2006.01)

(52) U.S. Cl. ........ 800/284; 800/278; 800/290; 800/295; 435/320.1; 435/69.1; 435/468; 435/183; 435/194; 536/23.1; 536/23.2; 536/23.6

(58) Field of Classification Search ........................ None
See application file for complete search history.

(56) References Cited

FOREIGN PATENT DOCUMENTS

| JP | 63-14693 | 11/1994 |
|---|---|---|
| WO | WO 87/06261 | 10/1987 |

OTHER PUBLICATIONS

Dawson et al. "A Tobacco Mosaic Virus-Hybrid Expresses and Loses an Added Gene", Virology, 172: 285-292, 1989.
French et al. "Bacterial Gene Inserted in an Engineered RNA Virus: Efficient Expression in Monocotyledonous Plant Cells", Science, 231: 1294-1297, 1986.
Horsch et al. "Leaf Disc Transformation", Plant Molecular Biological Manual, A5: 1-9, 1988.
Klee et al. "Agrobacterium-Mediated Plant Transformation and Its Further Applications to Plant Biology", Annual Reviews of Plant Physiology, 38: 467-486, 1987.
Klein et al. "Factors Influencing Gene Delivery Into Zea Mays Cells by High-Velocity Microprojectiles", Bio/Technology, 6: 559-563, 1988.
McCabe et al. "Stable Transformation of Soybean (Glycine Max) by Particle Acceleration", Bio/Technology, 6: 923-926, 1988.
Murray et al. "Codon Usage in Plant Genes", Nucleic Acids Research, 17(2): 477-498, 1989.
Odell et al. "Identification of DNA Sequences Required for Activity of the Cauliflower Mosaic Virus 35S Promoter", Nature, 313(6005): 810-812, 1985.
Ohta "High-Efficiency Genetic Transformation of Maize by a Mixture of Pollen and Exogenous DNA", Proc. Natl. Acad. Sci. USA, 83: 715-719, 1986.
Potrykus "Gene Transfer to Plants", Annual Review of Plant Physiology & Plant Molecular Biology, 42: 205-225, 1991.
Sanford "Biolistic Plant Transformation", Physiologia Plantarum, 79: 206-209, 1990.
Shimamoto "Fertile Transgenic Rice Plants Regenerated From Transformed Protoplasts", Nature, 338: 274-276, 1989. Abstract.
Takamatsu et al. "Expression of Bacterial Chloramphenicol Acetyltransferase Gene in Tobacco Plants Mediated by TMV-RNA", The EMBO Journal, 6(2): 307-311, 1987.
Takamatsu et al. "Production of Enkephalin in Tobacco Protoplasts Using Tobacco Mosaic Virus RNA Vector", FEBS, 269(1): 73-76, 1990.
Zhang et al. "Transgenic Rice Plants Produced by Electroporation-Mediated Plasmid Uptake Into Protoplasts", Plant Cell Reports, 7: 379-384, 1988.
Toriyama et al. "Transgenic Rice Plants After Direct Gene Transfer Into Protoplasts", Bio/Technology, 6: 1072-1074, 1988.

*Primary Examiner* — Medina A Ibrahim
*Assistant Examiner* — Brent Page

(57) ABSTRACT

A method of increasing biomass, vigor and/or yield of a plant is disclosed. The method comprises expressing within the plant an exogenous polypeptide comprising a UGGPase activity. The polypeptide may comprise an amino acid sequence at least 90% homologous, and/or at least 80% identical to SEQ ID NO: 33 as determined using the BlastP software of the National Center of Biotechnology Information (NCBI) using default parameters. Polynucleotides encoding same and plants expressing same are also disclosed.

13 Claims, 10 Drawing Sheets
(5 of 10 Drawing Sheet(s) Filed in Color)

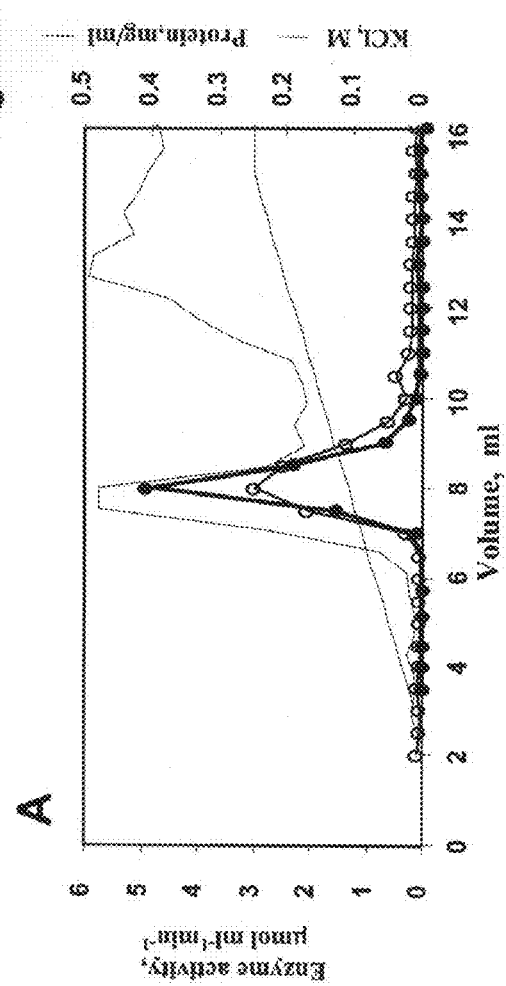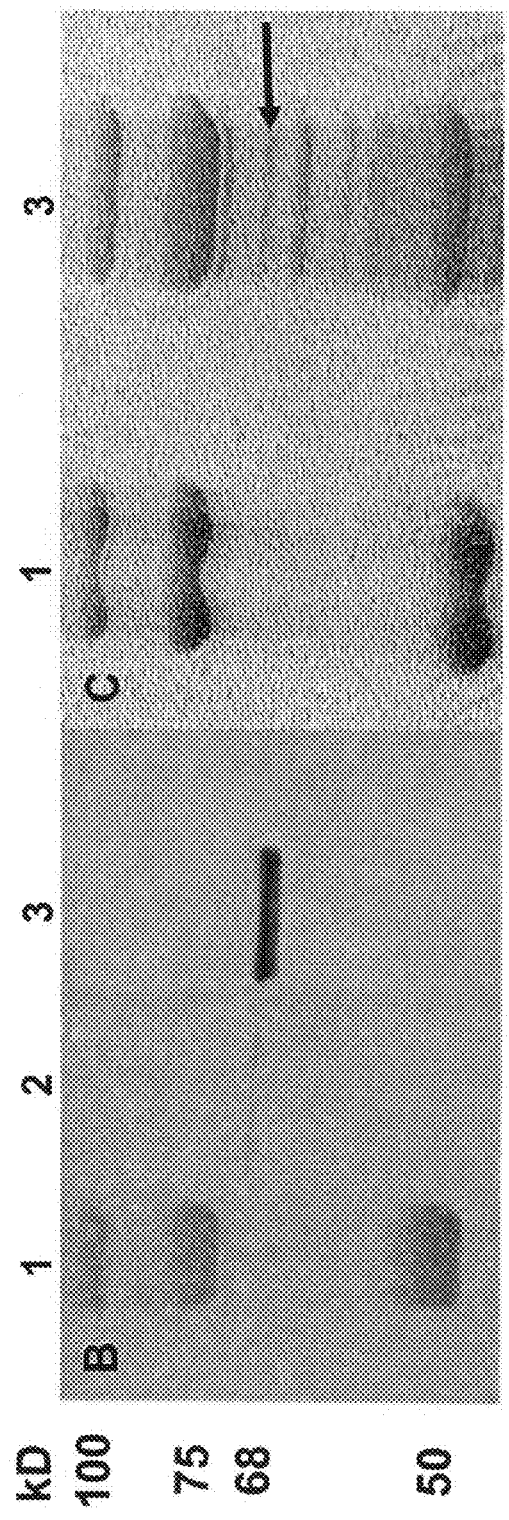
Figure 1

Figure 2A    Plant UGGPase

```
Melon  MASSLDSAALTLSNLSINGDFASSLPNLQKNLHLLSPQQVELAKILLELGQSHLFEHWAE            60
A.t.   MASTVDS-------------NFFSSVPALHSNLGLLSPDQIELAKILLENGQSHLFQQWPE            48
Pea    MASSLGD-------------NFNLLSPQQRELVKMLLDNGQDHLFRDWPN                       37
       *:**: .              .*  :* :. * :* .*::.  :****.: *

Melon  PGVDDNEKKAFFDQVARLNSSYPGGLASYIKTARGLLADSKEGKNPFDGFTPSVPTGEVL            120
A.t.   LGVDDKEKLAFFDQIARLNSSYPGGLAAYIKTAKELLADSKVGKNPYDGFSPSVPSGENL            108
Pea    PGVDDDEKKAFFDQLVLLDSSYPGGLVAYINNAKRLLADSKAGNNPFDGFTPSVPTGETL             97
       *****:** ****:. **.*******.** :: :::*****.*:**:****:***:** *

Melon  TFGDDSFVSFEDRGVREARKAAFVLVAGGLGERLGYNGIKVALPAETTTGTCFLQSYIEY            180
A.t.   TFGTDNFIEMEKRGVVEEARNAAFVLVAGGLGERLGYNGIKVALPRETTTGTCFLQHYIES            168
Pea    KFGDENFNKYEEAGVREARRAAFVLVAGGLGERLGYNGIKVALPAETTTGTCFLQHYIES            157
       .**.:.*:. *:.** *.*:*****************:***** *********:***:

Melon  VLALREASNRLAGE-SETEIPFVIMTSDDTHTRTVELLESNSYFGMKPSQVKLLKQEKVA           239
A.t.   ILALQEASNKIDSDSGSERDIPFIIMTSDDTHSRTLDLLELNSYFGMKPTQVHLLKQEKVA          228
Pea    ILALQEASSEGEGQ---THIPFVIMTSDDTHGRTLDLLESNSYFGMQPTQVTLLKQEKVA           214
       :***:***.. .    . :***:********.**:::**:*****:*:** *********

Melon  CLDDNEARLAVDPHNKYRIQTKPHGHGDVHALLYSSGLLKNWHNAGLRWVLFFQDTNGLL          299
A.t.   CLDDNDARLALDPHNKYSIQTKPHGHGDVHSLLYSSGLLHKWLEAGLKWVLFFQDTNGLL          288
Pea    CLEDNDARLALDPQNRYRVQTKPHGHGDVHSLLHSSGILKVWYNAGLKWVLFFQDTNGLL          274
       **:**:****:**:*:* :**********:** ***:::* ..***:************

Melon  FKAIPASLGVSATREYHVNSLAVPRKAKEAIGGITRLTHTDGRSMVINVEYNQLDPLLRA          359
A.t.   FNAIPASLGVSATKQYHVNSLAVPRKAKEAIGGISKLTRLTHVDGRSMVINVEYNQLDPLLRA       348
Pea    FKAIPSALGVSSTKQYHVNSLAVPRKAKEAIGGITRLTHSDGRSMVINVEYNQLDPLLRA          334
       *:***:.****:*::**************************::***:***************

Melon  TGFPDGDVNNETGYSPFPGNINQLILELGSYIEELSKTQGAIKEFVNPKYKDATKTSFKS          419
A.t.   SGFPDGDVNCETGFSPFPGNINQLILELGPYKDELQKTGGAIKEFVNPKYKDSTKTAFKS          408
Pea    SGYPDGDVNSETGYSPFPGNIQLILELAKTGGAIQEFVNPKYKDASKTSFKS                  394
       :*:******  ***:******:******. :: :**.**:***********:.**:***

Melon  STRLECMMQDYPKTLPPSARVGFTVMDTWVAYAPVKNNPEDAAKVPKGNPYHSATSGEMA          479
A.t.   STRLECMMQDYPKTLPFTARVGFTVMDIWLAYAPVKNNPEDAAKVPKGNPYHSATSGEMA          468
Pea    STRLECMMQDYPKTLPPSSRVGFTVMETWFAYAPVKNNAEDAAKVPKGNPYHSATSGEMA          454
       ****************  :******: *.*******.*****************:****

Melon  IYRANSLVLRKAGVKVADPVEQVFNGQEVEVWPRITWKPKWGLTFSEIKSKINGNCSISP          539
A.t.   IYRANSLILQKAGVKVEEPVKQVLNGQEVEVSRITWKPKWGMIFSDIKKKVSGNCEVSQ           528
Pea    IYRANSLILKKAGFQVADPVLQVINGQEVEVWPRITWKPKWGLTFSLVKSKVSGNCSISQ          514
       *******:*:***.:*::** **:******* *********:.** :*.*:.**.:*

Melon  RSTLVIKGKNVYLKDLSLDGTLIVNADEDAEVKVEGSVHNKGWTLEPVDYKDTSVPEEIR          599
A.t.   RSTMAIKGRNVFIKDLSLDGALIVDSIDDAEVKLGGLIKNNGWTMESVDYKDTSVPEEIR          588
Pea    RSTLAIKGRKIFIENLSVDGALIVDAVDDAEVNVSGSVQNNGWALEPVDYKDSSEPEVLR          574
       ***: ***::::.::*.**:***::  *****.: * ::*:**:: ******:* **:*

Melon  IRGFRINKIEQEERN--------  614
A.t.   IRGFRFNKVEQLEKKLTQPGKFSVED  614
Pea    IRGFKFNKVEQVEKKYSEPGKFDFKA  600
       ****::**:**  ::
```

Figure 2B  Plant UT

```
Melon   MASPVE------------SRRPELRKDSVTNRWVIFSPARAKRPSDFKSKS-PAPSSTD    46
Potato  MAEAETP-----------NRSPEIRKDKIHNRWVLFSPARSRRPSDFKAKSNPQP---N    45
A.t.    MTSPSHASDRGGGDGDSVENQSPELRKDPVTNRWIFSPARAKRPTDFKSKSPQNPN---P   58

Melon   SPQTCPFCIGQEHHCAPEIFRFPPQNP-DWKVRVIQNLYPALSRDKDLDSSTSLSSGSLL   105
Potato  NQTECPFCAGHEHECAPEIFRFRVPADSTNDWKIRVIQNLYPAVSRELDFQNPVSLVG---  101
A.t.    KPSSCPFCIGREQECAPELFRVPDHDP-NWKLRVIENLYPALSRNLETQSTQPETG----  113

Melon   WGCLLDGYGFHDVIIESPVHSVHLSDLTPEDVAQVLFAYKKRILQLASDDSIKYVQVFKN   165
Potato  -DVAVSGFGFHDVVIESPVHSVNLSDLSPAQVGEVLLACKKRIEQLRSCDSIKYVQVFKN   160
A.t.    TSRTIVGFGFHDVVIESPVHSIQLSDIDPVGIGDILIAYKKRINQIAQHDSINYIQVFKN   173

Melon   HGASAGASMTHPHSQMVGLPVIPPSVTTRLDSMKQYFNETGKCSICHVPTKDLLVDESVH   225
Potato  HGASAGASMSHSHSQMIALPIVPPTVSARLDSMMEYYKQTGKCSLCDIQPNELLIAESDH   220
A.t.    QGASAGASMSHSHSQMMALPVVPPTVSSRLDGTKDYFEETGKCCLCEAKSKHFVIDESSH   233

Melon   FISVVPYAASFPFELWIVPRDHVSHFHELDQEKAVDLGGLLKVTLIKMSLQLNKPPFNFM   285
Potato  FISLVPFAATFAFEIWIIPRDHSSHFHEIDSEKAVDLGGLLKLMLLKMSLQLNNPPFNLL   280
A.t.    FVSVAPFAATYPFEIWIIPKDHSSHFHHLDDVKAVDLGGLLKLMLQKIAKQLNDPPYNYM   293

Melon   IHTSPLQASDSDLAYSHWFFQIVPHLSGVGGFELGTGCYINPVFPEDAAKVMREVNISI-   344
Potato  IHTSPFQDDPSYAHSTHWFLQIAPHLSGVGGFEIATGCYINPVFPEDAAKILRDVRISNN   340
A.t.    IHTSPLKVTESQLPYTHWFLQIVPQLSGVGGFEIGTGCYINPVFPEDVAKVMREVSLTI-   351
```

Figure 2C    Plant UGPase

```
Melon    MASAATLSPADTEKLSKLKASVSGLTQISENEKSGFINLVSRYLSGEAQHVEWSKIQTPT   60
A.t.     -----MAATATEKLPQLKSAVDGLTEMSENEKSGFINLVSRYLSGEAQHIEWSKIQTPT   54
Potato   MVTATTLSPADAEKLNNLIKSAVAGLNQISENEKSGFINLVGRYLSGEAQHIDWSKIQTPT   60
Barley   ---MAAAAVAADSKIDGLRDAVAKLGEISENEKAGFISLVSRYLSGEAEQIEWSKIQTPT   57
             :    :    :: ** * :  :  *  ::*****:***.**.*****:*::****

Melon    DEVVVPYDSLAPVPNDPAETKKLLDKLVVLKLNGGLGTTMGCTGPKSVIEVRNGLTFLDL  120
A.t.     DEIVVPYDKMANVSEDASETKYLLDKLVVLKLNGGLGTTMGCTGPKSVIEVRDGLTFLDL  114
Potato   DEVVVPYDKLAPLSEDPAETKKLLDKLVVLKLNGGLGTTMGCTGPKSVIEVRNGLTFLDL  120
Barley   DEVVVPYDTLAPPPEDLDAMKALLDKLVVLKLNGGLGTTMGCTGPKSVIEVRNGFTFLDL  117
         **:*****.    . :  :  ::**********************:****:*:*****

Melon    IVIQIENLNSKYGCNVPLLLMNSFNTHDDTQKIIEKYKGSNVDIHTFNQSYPRLVAEDY  180
A.t.     IVIQIENLNNKYNCKVPLLVLMNSFNTHDDTQKIVEKYTKSNVDIHTFNQSKYPRVVADEF  174
Potato   IVKQIEALNAKFGCSVPLLLMNSFNTHDDTLKIVEKYANSNIDIHTFNQSYPRLVTEDF  180
Barley   IVIQIESLNKKYGCSVPLLLMNSFNTHDDTQKIVEKYSNSNIEIHTFNQSYPRIVTEDF  177
         ** ***.**.*:.*.***::**********.**:****. **:******* **:* *:

Melon    LPLPSKGRTDKDGWYPPGHGDVFPSLKNSGKLDALIAQGKEYVFVANSDNLGAVVDLQIL  240
A.t.     VPWPSKGKTDKDGWYPPGHGDVFPSLMNSGKLDAFLSQGKEYVFIANSDNLGAIVDLKIL  234
Potato   APLPCKGNSGKDGWYPPGHGDVFPSLMNSGKLDALLAKGKEYVFVANSDNLGAIVDLKIL  240
Barley   LPLPSKGQTGKDGWYPPGHGDVFPSLNNSGKLDTLLSQGKEYVSNEIHTFNQSYPRIVTEDF  237
          * *.**:  *************** ******:   :*****  :  .**.* :  :

Melon    NHLIQNKNEYCMEVTPKTLADVKGGTLISYEGKVQLLEIAQVPDEHVNEFKSIQKFKIFN  300
A.t.     KHLIQNKNEYCMEVTPKTLADVKGGTLISYEGKVQLLEIAQVPDEHVNEFKSIEKFKIFN  294
Potato   NHLILNKNEYCMEVTPKTLADVKGGTLISYEGKVQLLEIAQVPDEHVNEFKSIEKFKIFN  300
Barley   NHLIHNQNEYCMEVTPKTLADVKGGTLISYEGKVQLLEIAQVPDEHVDEFKSIEKFKIFN  297
         :**: *:************************************.***** ******

Melon    TNNLWVNLKAIKRLVEANALKMEIIPNPKEVDGIKVLQLETAAGAAIRFFDHAIGINVPR  360
A.t.     TNNLWVNLKAIKKLVEADALKMEIIPNPKEVDGVKVLQLETAAGAAIRFFDNAIGVNVPR  354
Potato   TNNLWVNLSAIKRLVEADALKMEIIPNPKEVDGVKVLQLETAAGAAIKFFDRAIGANVPR  360
Barley   TNNLWVNLKAIKRLVDAEALKMEIIPNPKEVDGVKVLQLETAAGAAIRFFEKAIGINVPR  357
         ******** ***:**.*:**************:*************:**: ***.****

Melon    SRFLPVKATSDLLLVQSDLYTLVDG-FVLRNKARKDPSNPSIELGPEFKKVGNFLSRFKS  419
A.t.     SRFLPVKATSDLLLVQSDLYTLVDG-FVTRNKARTNPTNPAIELGPEFKKVASFLSRFKS  413
Potato   SRFLPVKATSDLLLVQSDLYTLTDEGYVIRNPARSNPSNPSIELGPEFKKVANFLGRFKS  420
Barley   SRFLPVKATSDLLLVQSDLYTLVDG-YVIRNPARVKPSNPSIELGPEFKKVANFLARFKS  416
         **********************.*   * **.**  *:**:***********..**.***

Melon    IPSIIELDSLKVVGDVSFGAGVVLKGKVTISAKPGTKLAVPDNAVIANKEINGPEDF   476
A.t.     IPSIVELDSLKVSGDVWFGSGVVLKGKVTVKANAGTKLEIPDNAVLENKDINGPEDL   470
Potato   IPSIIDLDSLKVTGDVWFGSVTLKGKVTVAAKSNPVKLEIPDGAVIANKDINGPEDI   477
Barley   IPSIVELDSLKVSGDVSFGSVVLKGKVTIAAKSAGVKLEIPDGAVLENKDINGPEDI   473
         ****::****** *** **.  :*****:.**.  .** :** **:.**:*****
```

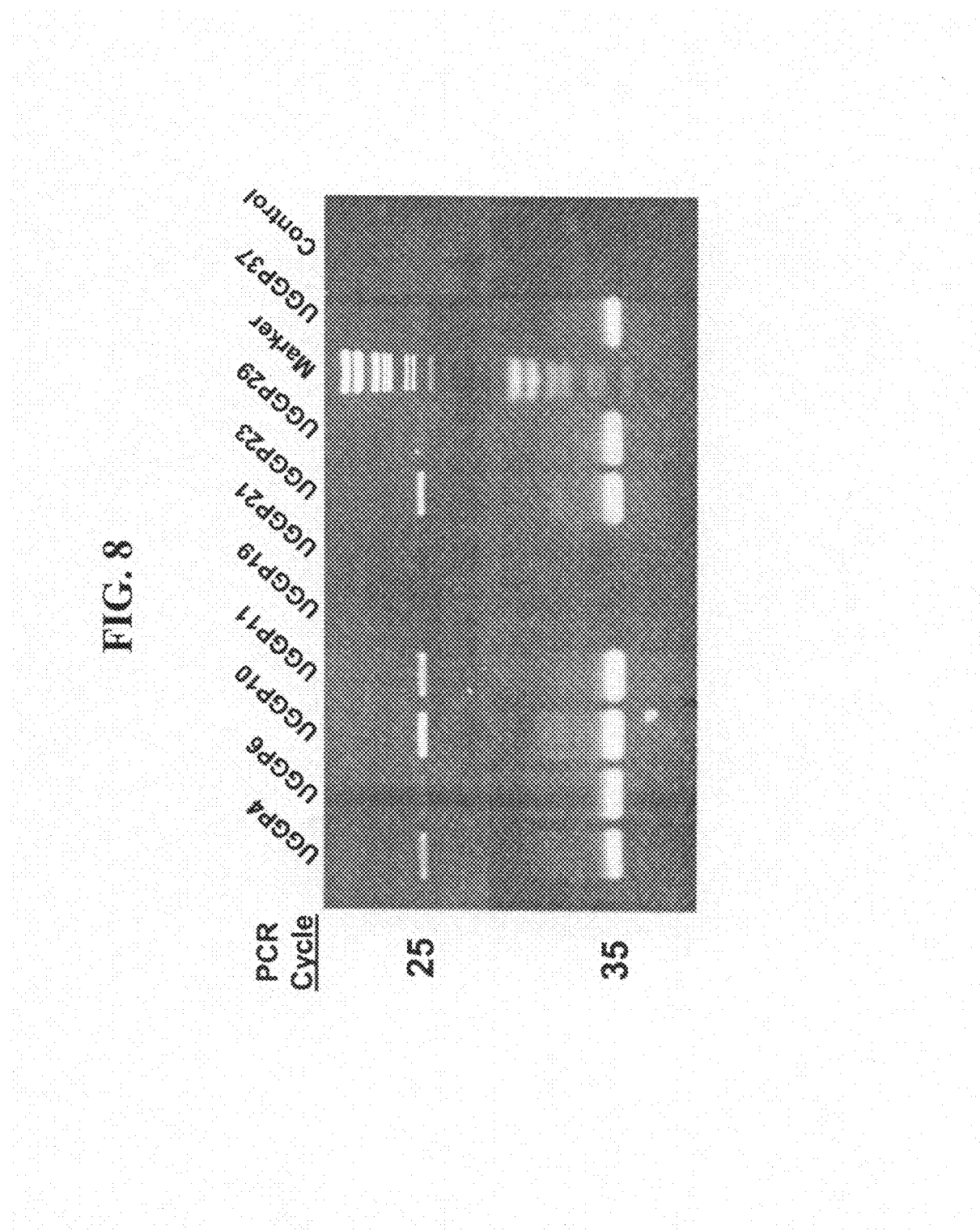

POLYNUCLEOTIDES AND POLYPEPTIDES ENCODED THEREFROM AND METHODS OF USING SAME FOR INCREASING BIOMASS IN PLANTS AND PLANTS GENERATED THEREBY

RELATED APPLICATIONS

This Application claims the benefit of U.S. Provisional Patent Application No. 60/817,687 filed on Jul. 3, 2006, the contents of which are hereby incorporated in its entirety.

FIELD AND BACKGROUND OF THE INVENTION

The present invention relates to methods of increasing biomass in plants and plants generated thereby.

Plants specifically improved for agriculture, horticulture, biomass conversion, and other industries (e.g. paper industry, plants as production factories for proteins or other compounds) can be obtained using molecular technologies.

Availability and maintenance of a reproducible stream of food and animal feed to feed animals and people has been a high priority throughout the history of human civilization and lies at the origin of agriculture. Specialists and researchers in the fields of agronomy science, agriculture, crop science, horticulture, and forest science are even today constantly striving to find and produce plants with an increased growth potential to feed an increasing world population and to guarantee a supply of reproducible raw materials. The robust level of research in these fields of science indicates the level of importance leaders in every geographic environment and climate around the world place on providing sustainable sources of food, feed, chemicals and energy for the population.

Manipulation of crop performance has been accomplished conventionally for centuries through plant breeding. The breeding process is, however, both time-consuming and labor-intensive. Furthermore, appropriate breeding programs must be specially designed for each relevant plant species.

On the other hand, great progress has been made in using molecular genetic approaches to manipulate plants to provide better crops. Through introduction and expression of recombinant nucleic acid molecules in plants, researchers are now poised to provide the community with plant species tailored to grow more efficiently and produce more product despite unique geographic and/or climatic environments. These new approaches have the additional advantage of not being limited to one plant species, but instead being applicable to multiple different plant species (Zhang et al. (2004) Plant Physiol. 135:615).

Despite this progress, today there continues to be a great need for generally applicable processes that improve forest or agricultural plant growth to suit particular needs depending on specific environmental conditions.

Cellulose, the most abundant organic polymer in the world, is deposited in the stems of plants and is extensively utilized for fuel, timber, forage, fibre and chemical cellulose.

Cellulose synthesis, in contrast with starch, is essentially an irreversible sink. Cellulose is produced from the precursor UDP-glucose, which can be formed via two potential pathways. UDP-glucose can be derived from the cleavage of sucrose in a reaction catalyzed by sucrose synthase (SuSy; EC 2.4.1.13) yielding UDP-glucose and fructose. Alternatively, UDP-glucose can be generated from the phosphorylation of glucose-1-phosphate in a reaction catalyzed by UDP-glucose pyrophosphorylase (UGPase, EC 2.7.7.9).

Another potential source of UDP-glucose is galactose. The entry of free galactose into metabolism begins with its phosphorylation by galactokinase (EC 2.7.1.6) to Gal-1-P. Following phosphorylation, two alternative pathways exist for the fate of the Gal-1-P in plants. One pathway is via the Leloir reaction, carried out by a uridyltransferase (UT, UDP-Glc: Hexose-1-P uridyltransferase, EC 2.7.7.12) utilizing UDP-Glc in a transferase reaction. However, this enzyme is generally not observed in most plants.

In an alternative pathway, Gal-1-P may be converted into UDP-Gal via a pyrophosphorylase (PPase, Gal-1-P: UTP transferase) utilizing UTP:

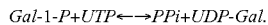

Gal-1-P+UTP←→PPi+UDP-Gal.

The UDP-Gal product of this pathway is further metabolized to UDP-Glc via the epimerase reaction.

Previous studies have shown that the melon fruit, with its active Gal metabolism, shows little UT activity, suggesting that a PPase is responsible for Gal-1-P metabolism [Smart and Pharr, 1981, Planta 153: 370-375; Feusi et al., 1999, Physiol Plant 106: 9-16]. There is no known PPase that is specific for the Gal moiety in melon fruit [Smart and Pharr, 1981, Planta 153: 370-375; Feusi et al., 1999, Physiol Plant 106: 9-16]. Rather, there appears to be a PPase in melon fruit which can utilize both Gal-1-P and Glc-1-P. This dual substrate PPase is present in cucurbit fruit in addition to the UGPase (UDP-Glc PPase, E.C. 2.7.7.9) which is specific for the Glc-1-P sugar, and inactive with Gal-1-P [Smart and Pharr, 1981, Planta 153: 370-375; Feusi et al., 1999, Physiol Plant 106: 9-16; Gao et al., 1999, Physiol Plant 106: 1-8]. Feusi et al. (1999) purified and characterized an enzyme fraction from melon fruit which catalyzed the nucleotide transfer to both Glc-1-P and Gal-1-P and were unable to further separate the activities, suggesting that the two reactions are catalyzed by the same protein (a UGGPase).

A UGGPase enzyme was described in germinating pea seeds (Kotake et al., 2004, J Biol Chem. 2004 October 29;279 (44):45728-36). The enzyme catalyzed the formation of UDP-Glc, UDP-Gal, UDP-glucuronic acid, UDP-1-arabinose, and UDP-xylose from respective monosaccharide 1-phosphates in the presence of UTP as a co-substrate, indicating that the enzyme has broad substrate specificity toward monosaccharide 1-phosphates.

It has been shown that there is a correlation between plant cellulose content and overall biomass. For example, a gene for UDP-glucose pyrophosphorylase has been cloned, and sense constructs inserted in tobacco plants. Heightened enzyme activity and cellulose synthesis were reported [Xue et al. 1997, Plant Physiol. 114(suppl 3):300]. Analyses indicated a 30% enhancement of cellulose content and a 20% increase in biomass. In addition, Coleman et al [Plant Biotechnology Journal. 4: 87-101, 2006] teach transgenic expression of UDP-Glc PPase in aspen trees and show a significant increase in plant height and biomass.

There is thus a widely recognized need for, and it would be highly advantageous to identify novel enzymes which utilize both glucose and galactose substrates for increasing cellulose content and biomass in plants.

SUMMARY OF THE INVENTION

According to one aspect of the present invention there is provided an isolated polynucleotide comprising a nucleic acid sequence encoding a polypeptide having an amino acid sequence at least 90% homologous, and/or at least 80% identical to SEQ ID NO: 33 as determined using the BlastP software of the National Center of Biotechnology Information (NCBI) using default parameters, wherein the polypeptide comprises a UDP glucose/galactose pyrophosphorylase (UGGPase) activity.

According to another aspect of the present invention there is provided an isolated polypeptide comprising an amino acid sequence at least 90% homologous, and/or at least 80% identical to SEQ ID NO: 33 as determined using the BlastP software of the National Center of Biotechnology Information (NCBI) using default parameters, wherein the polypeptide comprises a UGGPase activity.

According to yet another aspect of the present invention there is provided an isolated polynucleotide comprising a nucleic acid sequence encoding a polypeptide as set forth in SEQ ID NO: 33.

According to an additional aspect of the present invention there is provided an isolated polynucleotide comprising a nucleic acid sequence as set forth in SEQ ID NO: 34.

According to yet an additional aspect of the present invention there is provided an isolated polynucleotide comprising a nucleic acid sequence encoding a polypeptide having an amino acid sequence at least 95% homologous, and/or at least 90% identical to SEQ ID NO: 35 as determined using the BlastP software of the National Center of Biotechnology Information (NCBI) using default parameters, wherein the polypeptide comprises a UDP glucose pyrophosphorylase (UGPase) activity.

According to still an additional aspect of the present invention there is provided an isolated polynucleotide comprising a nucleic acid sequence encoding a polypeptide as set forth in SEQ ID NO: 35.

According to a further aspect of the present invention there is provided an isolated polynucleotide comprising a nucleic acid sequence as set forth in SEQ ID NO: 36.

According to yet a further aspect of the present invention there is provided an isolated polypeptide comprising an amino acid sequence at least 95% homologous, and/or at least 90% identical to SEQ ID NO: 35 as determined using the BlastP software of the National Center of Biotechnology Information (NCBI) using default parameters, wherein the polypeptide comprises a UGPase activity.

According to still a further aspect of the present invention there is provided an isolated polypeptide comprising an amino acid sequence as set forth in SEQ ID NO: 35.

According to still a further aspect of the present invention there is provided an isolated polynucleotide comprising a nucleic acid sequence encoding a polypeptide having an amino acid sequence at least 85% homologous, and/or at least 75% identical to SEQ ID NO: 37 as determined using the BlastP software of the National Center of Biotechnology Information (NCBI) using default parameters, wherein the polypeptide comprises a uridyltransferase (UT) activity.

According to still a further aspect of the present invention there is provided an isolated polynucleotide comprising a nucleic acid sequence encoding a polypeptide as set forth in SEQ ID NO: 37.

According to still a further aspect of the present invention there is provided an isolated polynucleotide comprising a nucleic acid sequence as set forth in SEQ ID NO: 38.

According to still a further aspect of the present invention there is provided an isolated polypeptide comprising an amino acid sequence at least 85% homologous, and/or at least 75% identical to SEQ ID NO: 37 as determined using the BlastP software of the National Center of Biotechnology Information (NCBI) using default parameters, wherein the polypeptide comprises a UT activity.

According to still a further aspect of the present invention there is provided an isolated polypeptide comprising an amino acid sequence as set forth in SEQ ID NO: 38.

According to still a further aspect of the present invention there is provided a plant cell comprising an exogenous polypeptide comprising an amino acid sequence at least 90% homologous, and/or at least 80% identical to SEQ ID NO: 33 as determined using the BlastP software of the National Center of Biotechnology Information (NCBI) using default parameters, wherein the polypeptide comprises a UGGPase activity.

According to yet a further aspect of the present invention there is provided a plant cell comprising an exogenous polypeptide comprising an amino acid sequence at least 95% homologous, and/or at least 90% identical to SEQ ID NO: 35 as determined using the BlastP software of the National Center of Biotechnology Information (NCBI) using default parameters, wherein the polypeptide comprises a UGPase activity.

According to still a further aspect of the present invention there is provided a plant cell comprising an exogenous polypeptide comprising an amino acid sequence at least 85% homologous, and/or at least 75% identical to SEQ ID NO: 37 as determined using the BlastP software of the National Center of Biotechnology Information (NCBI) using default parameters, wherein the polypeptide comprises a UT activity.

According to still a further aspect of the present invention there is provided a method of increasing biomass, vigor and/or yield of a plant comprising expressing within the plant an exogenous polypeptide comprising a UGGPase activity, thereby increasing biomass, vigor and/or yield of the plant.

According to further features in preferred embodiments of the invention described below, the UGGPase activity comprises a higher affinity for a Glucose-1-phosphate than a Galactose-1-phophate.

According to still further features in the described preferred embodiments, the isolated polypeptide comprises a Km for Galactose-1-phosphate of about 0.43 mM.

According to still further features in the described preferred embodiments, the isolated polypeptide comprises a Km for Glucose-1-phosphate of about 0.27 mM.

According to still further features in the described preferred embodiments, the isolated polypeptide comprises a Km for UDP-Galactose of about 0.44 mM.

According to still further features in the described preferred embodiments, the isolated polypeptide comprises a Km for UDP-Glucose of about 0.14 mM.

According to still further features in the described preferred embodiments, a maximum enzyme velocity ($V_{max}$) of the UGGPase activity is higher for a Galactose-1-phosphate than a Glucose-1-phosphate.

According to still further features in the described preferred embodiments, the isolated polypeptide comprises a Vmax for Galactose-1-phosphate of about 714 µmol mg protein$^{-1}$min$^{-1}$.

According to still further features in the described preferred embodiments, the isolated polypeptide comprises a Vmax for Glucose-1-phosphate of about 222 µmol mg protein$^{-1}$min$^{-1}$.

According to still further features in the described preferred embodiments, the isolated polypeptide comprises a Vmax for UDP-Galactose of about 625 µmol mg protein$^{-1}$min$^{-1}$.

According to still further features in the described preferred embodiments, the isolated polypeptide comprises a Vmax for UDP-Glucose of about 238 µmol mg protein$^{-1}$ min$^{-1}$.

According to still further features in the described preferred embodiments, the isolated polypeptide comprises a higher enzymatic activity towards a galactose substrate than an enzymatic activity of a UGPase for a galactose substrate.

According to still further features in the described preferred embodiments, the polypeptide is capable of converting Gal-1-phosphate to UDP-Gal and further is capable of converting UDP-glucose to glucose-1-phosphate.

According to still further features in the described preferred embodiments, the isolated polypeptide comprises an amino acid sequence as set forth by SEQ ID NO: 33.

According to still further features in the described preferred embodiments, the plant cell forms a part of a plant.

According to still further features in the described preferred embodiments, the plant further comprises an exogenous UGPase.

According to still further features in the described preferred embodiments, the exogenous UGpase comprises an amino acid sequence as set forth in SEQ ID NO: 35.

According to still further features in the described preferred embodiments, the plant cell forms a part of a plant.

According to still further features in the described preferred embodiments, the exogenous polypeptide comprises an amino acid sequence at least 90% homologous, and/or at least 80% identical to SEQ ID NO: 33 as determined using the BlastP software of the National Center of Biotechnology Information (NCBI) using default parameters.

According to still further features in the described preferred embodiments, the expressing is effected by introducing to the plant a nucleic acid construct which comprises a polynucleotide sequence encoding the polypeptide and at least one promoter capable of directing transcription of the polynucleotide in the plant cell.

According to still further features in the described preferred embodiments, the at least one promoter is a constitutive promoter.

According to still further features in the described preferred embodiments, the at least one promoter is an inducible promoter.

According to still further features in the described preferred embodiments, the expressing is effected by infecting the plant with a virus.

According to still further features in the described preferred embodiments, the virus is an avirulent virus.

According to still further features in the described preferred embodiments, the method further comprises expressing within the plant an exogenous UGPase.

The present invention successfully addresses the shortcomings of the presently known configurations by providing polypeptides and polynucleotides encoding same, capable of upregulating plant growth and yield.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

The file of this patent contains at least one drawing executed in color photograph. Copies of this patent with color photograph(s) will be provided by the Patent and Trademark Office upon request and payment of necessary fee.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1A depicts partial purification of melon fruit UGGPase (SEQ ID NO: 33) on HPLC-MonoQ. Closed circles indicate activity with UDP-Glc in the pyrophosphorolytic direction and open circles indicate activity with Gal-1-P in the synthesis direction.

FIG. 1B depicts a Western blot using UGGPase antibodies (Feusi et al., 1999) of electrophoretic separations of MW markers (first lane), crude melon fruit extracts (second lane) and HPLC MonoQ fractions exhibiting UGGPase activity (third lane); FIG.1C, Coomassie Blue protein stain of the HPLC MonoQ fractions exhibiting UGGPase activity: MW markers (first lane) and HPLC MonoQ fractions exhibiting UGGPase activity (second lane). The band in the Coomassie stain, indicated by the arrow and corresponding to the band in the immunoblot, was excised and microsequenced.

FIGS. 2A-C are protein sequence homology alignments of plant UGGPase (SEQ ID NO: 33), UGPase (SEQ ID NO: 35) and UT (SEQ ID NO: 37). Sequences in bold indicate the seven peptide sequences (SEQ ID NOs: 39-45) obtained from the peptide microsequencing of the purified protein. Underlined sequences indicate conserved sequences used for the preparation of degenerate primers for the PCR cloning of the melon genes. Accession numbers of the sequence presented are: UGGPase: melon (DQ399739), Arabidopsis (AF360236), pea (AB178642); UT: melon DQ445484, potato (TC28197), Arabidopsis (NM__121825); UGPase: melon DQ445483, Arabidopsis (NM__121737), potato (U20345), barley (Q07131).

FIG. 3A); melon UGPase (SEQ ID NO: 35; FIG. 3B); and melon UT (SEQ ID NO: 37; FIG. 3C). For each enzyme the three lanes represent, respectively, the MW marker, the *E. coli* extract with the expressed protein (+IPTG) and the *E. coli* extract without the heterologously expressed protein (−IPTG).

FIG. 8 is a photograph illustrating UGGPase (SEQ ID NO: 33) expression level in independent transgenic plants following semi-quantitative RT-PCR in 25 and 35 cycles.

DESCRIPTION OF THE PREFERRED EMBODIMENTS

The present invention is of polypeptides and polynucleotides encoding same capable of increasing plant biomass and/or ethanol production.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Cellulose is produced from the precursor UDP-glucose, which can be formed via a number of enzymatic reactions, including via the cleavage of sucrose (in a reaction catalyzed by sucrose synthase (SuSy; EC 2.4.1.13)) and/or the phosphorylation of glucose-1-phosphate (in a reaction catalyzed by UDP-glucose pyrophosphorylase (UGPase, EC 2.7.7.9)). Following expression of UGPase in tobacco plants, heightened enzyme activity and cellulose synthesis were reported [Xue et al. 1997, Plant Physiol. 114(suppl 3):300].

Another potential source of UDP-glucose is galactose. Gal-1-P may be converted into UDP-Gal via a pyrophosphorylase (PPase, Gal-1-P: UTP transferase) utilizing UTP:

Gal-1-P+UTP↔PPi+UDP-Gal.

The UDP-Gal product of this pathway is further metabolized to UDP-Glc via the epimerase reaction.

Through meticulous experimentation, the present inventors cloned and sequenced the melon UGGPase (FIGS. 1-2A). This enzyme is capable of utilizing both glucose and galactose as a source of starting material for generating cellulose and showed that it was possible to induce the expression thereof in tobacco cell plants (FIG. 8).

In addition, the present inventors cloned and sequenced for the first time, melon UGPase (FIG. 2B) and melon uridyltransferase (UT; FIG. 2C), two enzymes which, in conjunction with expressing the UGGPase of the present invention, may further aid in increasing cellulose biomass.

Figure 3:
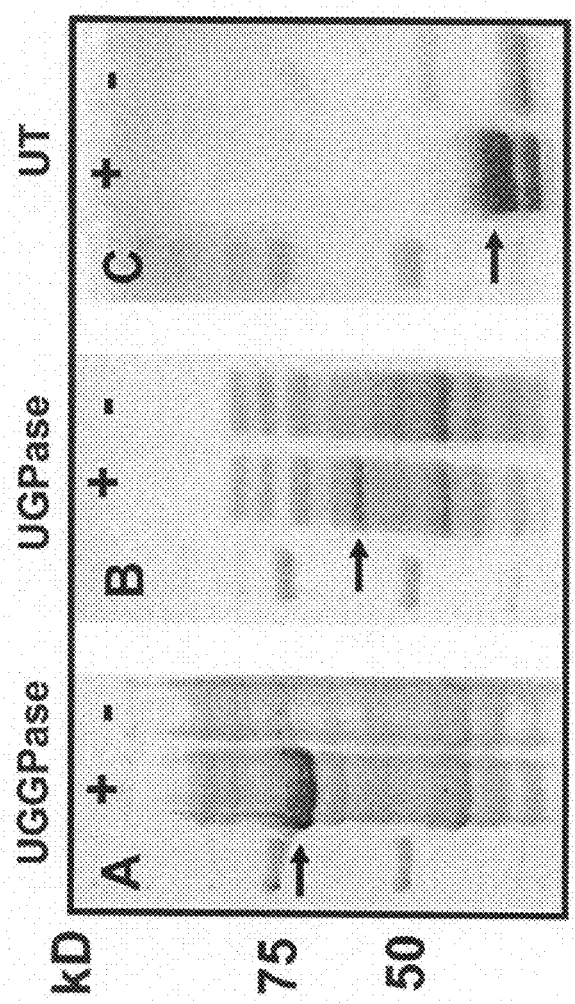
FIGS. 3A-C is a Coomassie stained SDS-PAGE gel loaded with an *E. coli* protein extract following heterologous expression of melon UGGPase (SEQ ID NO: 33.
Figure 5:
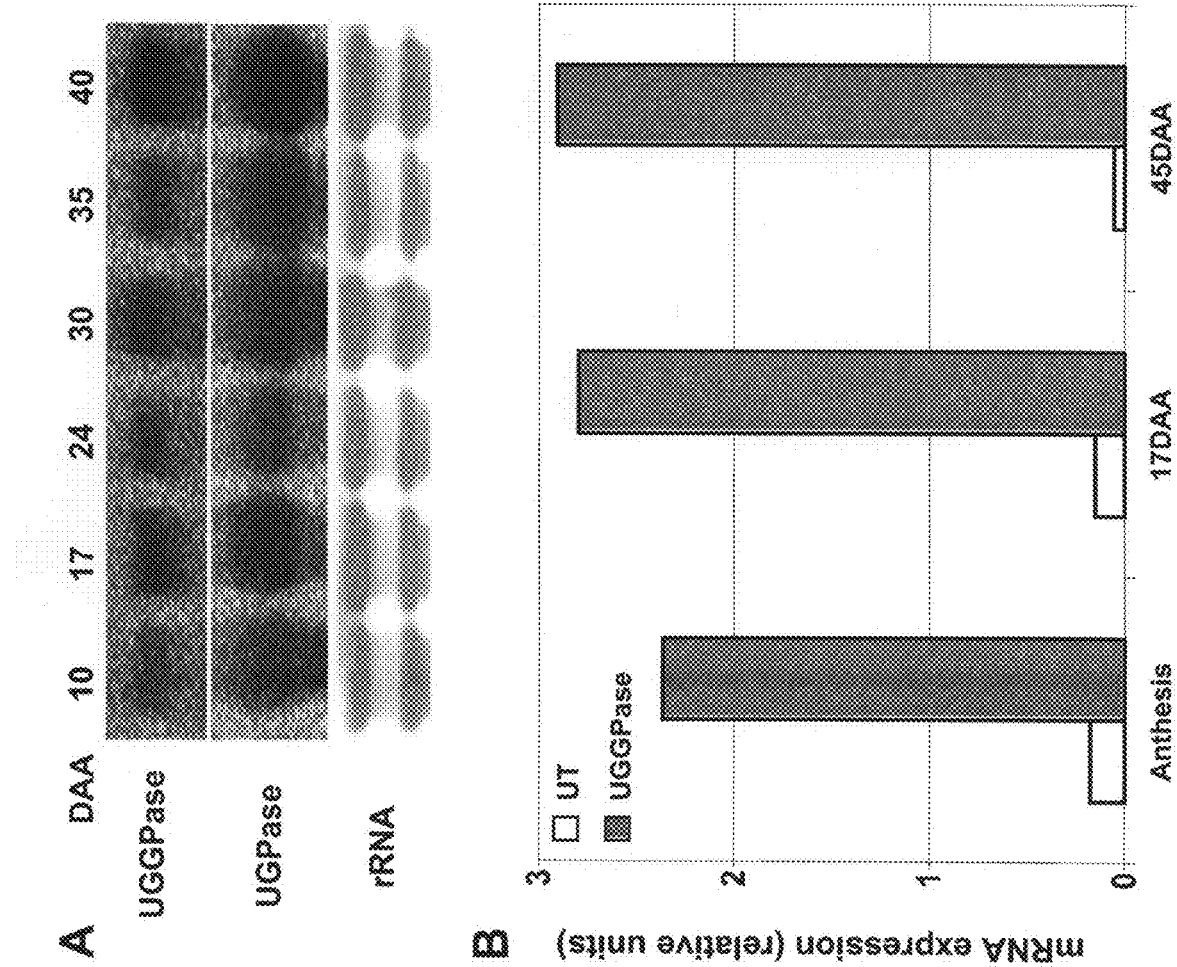
FIGS. 5A-B depict expression patterns of UGGPase (SEQ ID NO: 33), UGPase (SEQ ID NO: 35) and UT (SEQ ID NO: 37) in developing melon fruit by Northern blots (FIG. 5A; UT was not detected and is not presented) and by Quantitative RT-PCR of UT and UGGPase (FIG. 5B). mRNA expression is relative to the expression of the melon actin gene. DAA, days after anthesis; rRNA, ribosomal RNA.
Figure 6:
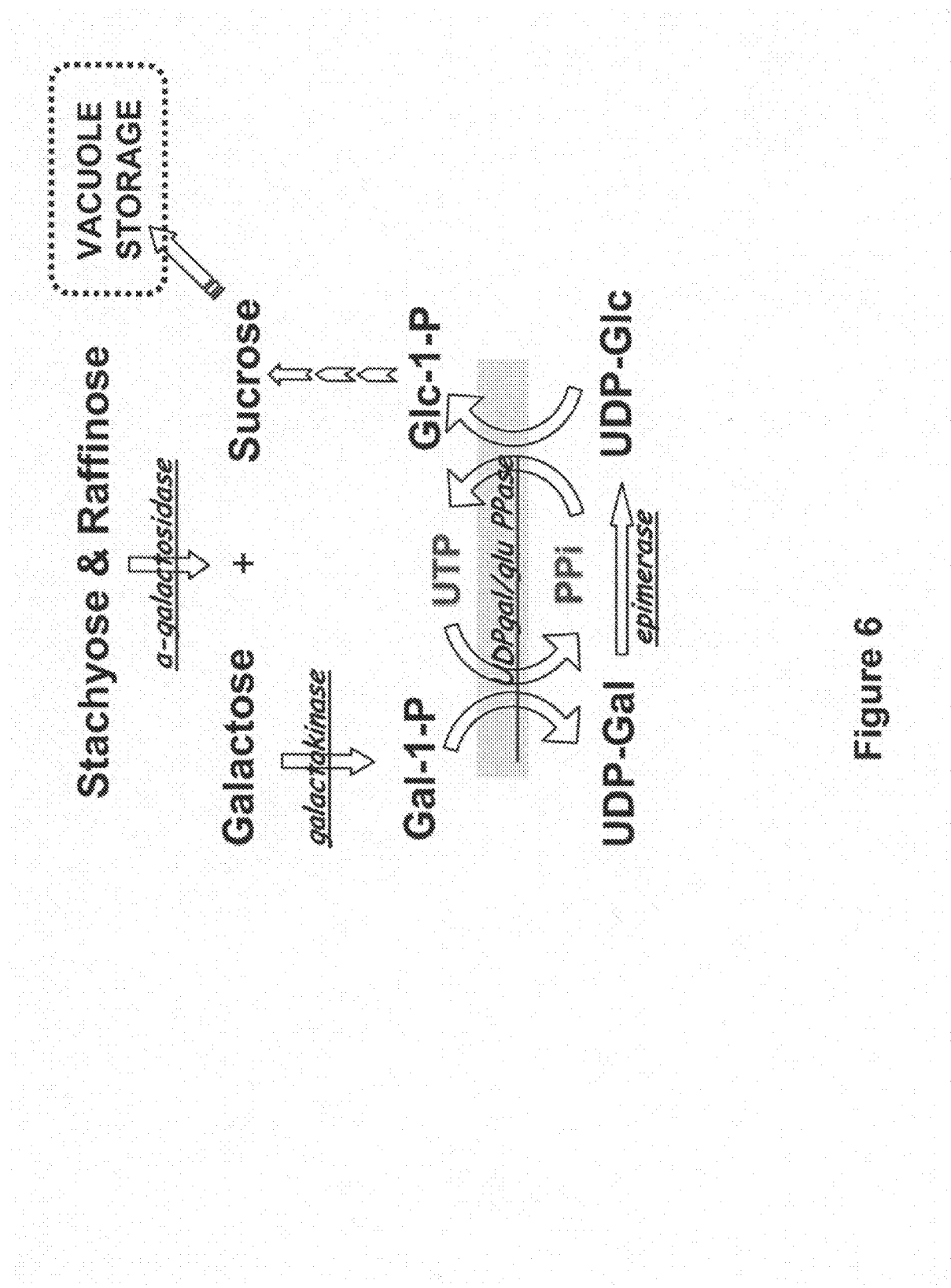
FIG. 6 is a schematic diagram of the proposed pathway of galactose metabolism in melon fruit, emphasizing the dual role of the UGGPase. The enzymes involved in galactose metabolism in melon fruit are represented in italics.
Figure 7:
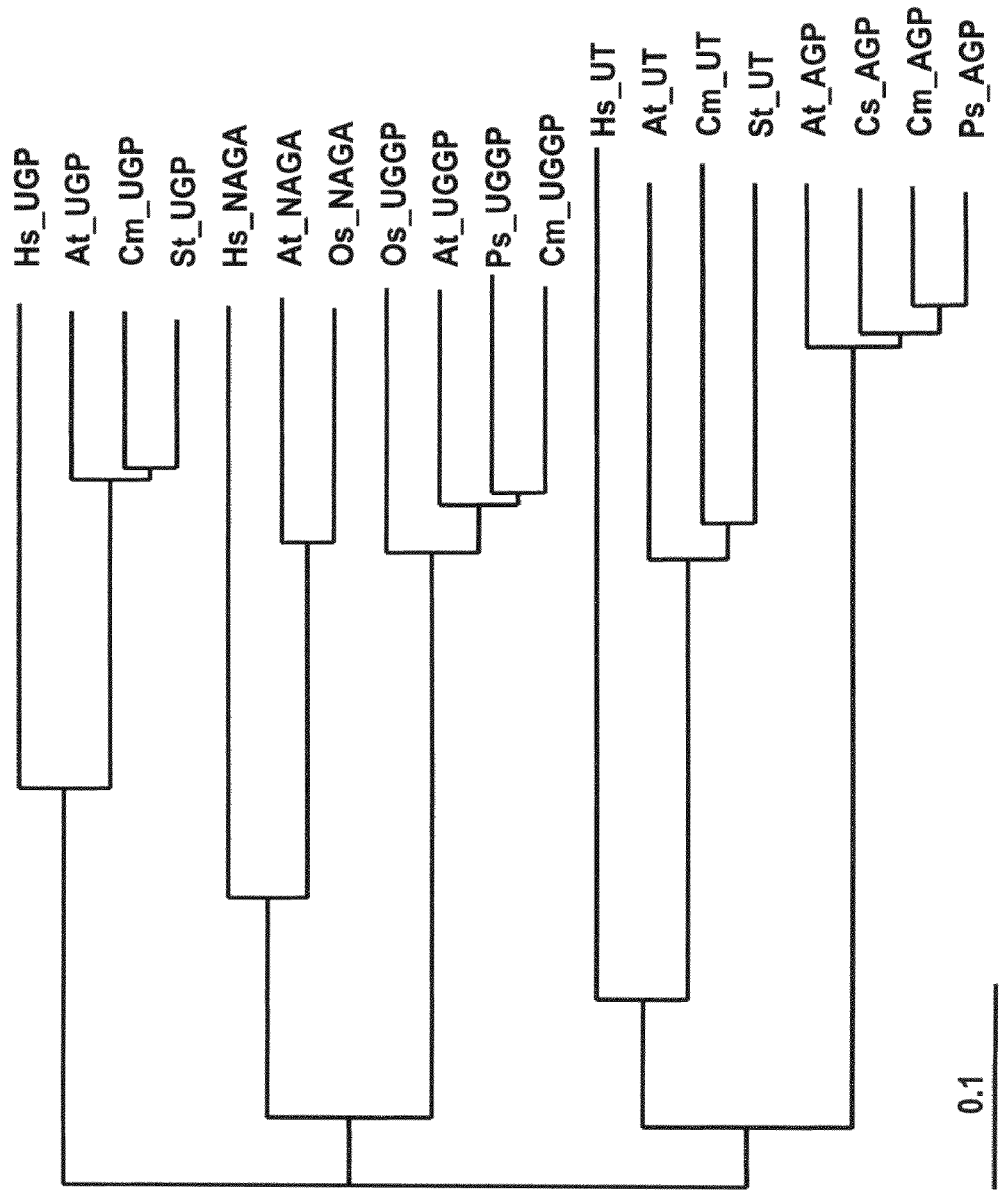
FIG. 7 is a phylogenetic tree of nucleotide-sugar metabolism enzymes. The abbreviations and the accession numbers of the sequences used in the preparation of the tree are as follows: UGP, UGPase: *Homo sapiens* (Hs), Q07131; *Arabidopsis thaliana* (At), NM_121737; *Cucumis melo* (Cm), DQ445483; *Solanum tuberosum* (St), U20345. NAGA, UDP-N-acetyl-Gal/Glc amine PPase: *Homo sapiens* (Hs), BC009377; *Arabidopsis thaliana* (At), BT020380; *Oryza sativa* (Os), AK071409. UGGP, UGGPase: *Oryza sativa* (Os), AK064009; *Arabidopsis thaliana* (At), AF360236; *Pisum sativum* (Ps), AB178642; *Cucumis melo* (Cm), DQ399739. UT, uridyltransferase: *Homo sapiens* (Hs), P07902; *Arabidopsis thaliana* (At), NM_121825; *Cucumis melo* (Cm), DQ445484; *Solanum tuberosum* (St), TC28197. AGP, ADPglu PPase, small subunit: *Arabidopsis thaliana* (At), NM_124205; *Citrus unshiu* (Cu), AF184597; *Cucumis melo* (Cm), AF030382; *Pisum sativum* (Ps), X96764. The tree was prepared using the Clustal X alignment and Treeview programs. Bar represents distance value of 0.1 substitution per site.

The three melon enzymes were bacterially expressed (FIGS. 3A-C) and characterized (FIGS. 5A-B and Tables 1-5).

Thus, according to one aspect of the present invention there is provided a method of increasing biomass, vigor and/or yield of a plant comprising expressing within the plant an exogenous polypeptide comprising a UGGPase activity. The present invention also contemplates expression of other homologues, orthologues and active portions of the above mentioned exogenous polypeptides as will be further described hereinbelow.

As used herein the phrase "plant biomass" refers to the amount or quantity of tissue (in particular cellulose comprising tissue) produced from the plant in a growing season, which could also determine or affect the plant yield or the yield per growing area.

As used herein the phrase "plant vigor" refers to the amount or quantity of (cellulose comprising) tissue produced from the plant in a given time. Hence increase vigor could determine or affect the plant yield or the yield per growing time or growing area.

As used herein the phrase "plant yield" refers to the amount or quantity of (cellulose comprising) tissue produced and harvested as the plant produced product. Hence increase yield could affect the economic benefit one can obtain from the plant in a certain growing time.

Methods of determining biomass, yield and vigor are well known in the art and further described in Coleman et al, 2006, Plant Biotechnology Journal 4 (1), 87-101.

As used herein the term "improving" or "increasing" refers to improving or increasing the biomass/yield/vigor of the transgenic plant of the present invention by at least about 2% more, 5% more, 10% more, 20% more, 30% more, 40% more, 50% more, 60% more, 70% more, 80% more, 90% or more than that of the non-transgenic plant (e.g., mock transfected, or naive).

The term "plant" as used herein encompasses whole plants, ancestors and progeny of the plants and plant parts, including seeds, shoots, stems, roots (including tubers), and plant cells, tissues and organs. The term "plant" also therefore encompasses suspension cultures, embryos, meristematic regions, callus tissue, leaves, gametophytes, sporophytes, pollen, and microspores. Plants that are particularly useful in the methods of the invention include all plants which belong to the super-family Viridiplantae, in particular monocotyledonous and dicotyledonous plants which are of commercial value, including a fodder or forage legume, ornamental plant, food crop, tree, or shrub selected from the following non-limiting list comprising maize, sweet potato, tubers such as cassarva, sugar beet, wheat, barely, rye, oat, rice, soybean, peanut, pea, lentil and alfalfa, cotton, rapeseed, canola, pepper, sunflower, potato, tobacco, tomato, eggplant, trees such as eucalyptus and poplars, an ornamental plant, a perennial grass and a forage crop.

As used herein, the term "exogenous polypeptide" refers to a polypeptide that is introduced into a cell by artifice, such that a level of expression thereof is greater than in an identical cell not comprising the exogenous polypeptide. The expressing is typically effected by introducing an exogenous polynucleotide encoding the polypeptide of the present invention into the plant either in a stable or transient manner as further described herein below.

As used herein, the phrase "UGGPase activity" refers to an enzyme capable of catalyzing the following two reactions:

$Gal\text{-}1\text{-}P+UTP \rightarrow PPi+UDP\text{-}Gal.$ $Glu\text{-}1\text{-}P+UTP \rightarrow PPi+UDP\text{-}Glu.$ According to one embodiment of this aspect of the present invention, the polypeptides of the present invention are also capable of catalyzing the reverse reactions, as follows:

$Gal\text{-}1\text{-}P+UTP \leftarrow PPi+UDP\text{-}Gal.$ $Glu\text{-}1\text{-}P+UTP \leftarrow PPi+UDP\text{-}Glu.$ According to one embodiment, the UGGPase activity (EC 2.7.7.64) of the polypeptide of the present invention comprises a higher affinity for a Glucose-1-phosphate than a Galactose-1-phophate.

Methods of determining protein affinity are well known in the art [e.g., BiaCore and/or Scatchard analyses (RIA)]. An exemplary method for determining the relative affinity for the substrates of the polypeptide of the present invention is described in the general materials and methods section herein below.

Thus, according to one embodiment, the concentration of Galactose-1-phosphate that leads to half-maximal velocity (Km) of the polypeptide of the present invention is about 0.43 mM.

According to another embodiment, the Km of the polypeptide of the present invention for Glucose-1-phosphate is about 0.27 mM.

According to still another embodiment, the Km of the polypeptide of the present invention for UDP-Galactose is about 0.44 mM.

According to yet another embodiment, the Km of the polypeptide of the present invention for UDP-Glucose is about 0.14 mM.

According to one embodiment, the polypeptide of the present invention comprises a higher enzymatic activity towards a galactose substrate (i.e. galactose-1-phosphate) than an enzymatic activity of a UGPase for a galactose substrate.

Methods of determining the enzymatic activity of the polypeptides of the present invention towards their glucose/galactose substrates are described in the materials and methods section herein below.

According to another embodiment, the maximum enzyme velocity ($V_{max}$) of the UGGPase activity of the polypeptide of the present invention is higher for a Galactose-1-phosphate than a Glucose-1-phosphate.

According to yet another embodiment, the Vmax for Galactose-1-phosphate of the polypeptide of the present invention is about 714 µmol mg protein$^{-1}$min$^{-1}$.

According to still another embodiment, the Vmax for Glucose-1-phosphate of the polypeptide of the present invention is about 222 µmol mg protein$^{-1}$min$^{-1}$.

According to yet another embodiment, the Vmax for UDP-Galactose of the polypeptide of the present invention is about 625 µmol mg protein$^{-1}$min$^{-1}$.

According to still another embodiment, the Vmax for UDP-Glucose of the polypeptide of the present invention is about 238 µmol mg protein$^{-1}$min$^{-1}$.

It will be appreciated that the method of increasing biomass of a plant may be effected by expressing any exogenous UGGPase in a plant including but not limited to the UGGPase isolated from pea seeds (Kotake et al., 2004, J Biol Chem. 2004 October 29;279(44):45728-36). The present inventors searched the EST databases (www.tigr.org) and showed that other plant families also express homologues of UGGPase. Such families include, but are not limited to Solanaceae (tomato, BF05177), Brassicaceae (Arabidopsis, TC262279), Leguminoseae (soya, TC228175), Compositaceae, (sunflower, TC10097), and Graminae (wheat, TC251010), although these are described as unknown proteins. Thus the present invention contemplates artificial expression of these proteins to increase biomass of a plant.

According to one embodiment of this aspect of the present invention, the exogenous polypeptide comprises an amino acid sequence at least 90% homologous, and/or at least 80% identical to SEQ ID NO: 33, which comprises a UGGPase activity. According to one embodiment the polypeptide comprises an amino acid sequence as set forth by SEQ ID NO: 33.

The present invention contemplates expression of any polynucleotide encoding a polypeptide with an amino acid sequence at least 90% homologous, and/or at least 80% identical to SEQ ID NO: 33. For example, the present invention contemplates expression of a polynucleotide of a sequence as set forth in SEQ ID NO: 34 encoding the polypeptide as set for the in SEQ ID NO: 33.

Thus, the a nucleic acid sequence is at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, or more say 100% identical to a nucleotide sequence selected from the group consisting of SEQ ID NO: 34.

Nucleic acid sequences may encode polypeptide sequences comprising an amino acid sequence at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, or more say 100% homologous to SEQ ID NO 33.

Homology (e.g., percent homology) can be determined using any homology comparison software, including for example, the BlastP software of the National Center of Biotechnology Information (NCBI) such as by using default parameters (as detailed above).

Identity (e.g., percent homology) can be determined using any homology comparison software, including for example, the BlastN software of the National Center of Biotechnology Information (NCBI) such as by using default parameters (as detailed above).

According to one preferred embodiment of this aspect of the present invention the isolated polynucleotide is as set forth in SEQ ID NO: 34.

A nucleic acid sequence (also termed herein as isolated polynucleotide) of the present invention refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

Nucleic acid sequences of the polypeptides of the present invention may be optimized for plant expression. Examples of such sequence modifications include, but are not limited to, an altered G/C content to more closely approach that typically found in the plant species of interest, and the removal of codons atypically found in the plant species commonly referred to as codon optimization.

The phrase "codon optimization" refers to the selection of appropriate DNA nucleotides for use within a structural gene or fragment thereof that approaches codon usage within the plant of interest. Therefore, an optimized gene or nucleic acid sequence refers to a gene in which the nucleotide sequence of a native or naturally occurring gene has been modified in order to utilize statistically-preferred or statistically-favored codons within the plant. The nucleotide sequence typically is examined at the DNA level and the coding region optimized for expression in the plant species determined using any suitable procedure, for example as described in Sardana et al. (1996, Plant Cell Reports 15:677-681). In this method, the standard deviation of codon usage, a measure of codon usage bias, may be calculated by first finding the squared proportional deviation of usage of each codon of the native gene relative to that of highly expressed plant genes, followed by a calculation of the average squared deviation. The formula used is: 1 SDCU=n=1 N[(Xn−Yn )/Yn]2/N, where Xn refers to the frequency of usage of codon n in highly expressed plant genes, where Yn to the frequency of usage of codon n in the gene of interest and N refers to the total number of codons in the gene of interest. A table of codon usage from highly expressed genes of dicotyledonous plants is compiled using the data of Murray et al. (1989, Nuc Acids Res. 17:477-498).

One method of optimizing the nucleic acid sequence in accordance with the preferred codon usage for a particular plant cell type is based on the direct use, without performing any extra statistical calculations, of codon optimization tables such as those provided on-line at the Codon Usage Database through the NIAS (National Institute of Agrobiological Sciences) DNA bank in Japan (http://www.kazusa.orjp/codon/). The Codon Usage Database contains codon usage tables for a number of different species, with each codon usage table having been statistically determined based on the data present in Genbank.

By using the above tables to determine the most preferred or most favored codons for each amino acid in a particular species (for example, rice), a naturally-occurring nucleotide sequence encoding a protein of interest can be codon optimized for that particular plant species. This is effected by replacing codons that may have a low statistical incidence in the particular species genome with corresponding codons, in regard to an amino acid, that are statistically more favored. However, one or more less-favored codons may be selected to delete existing restriction sites, to create new ones at potentially useful junctions (5' and 3' ends to add signal peptide or termination cassettes, internal sites that might be used to cut and splice segments together to produce a correct full-length sequence), or to eliminate nucleotide sequences that may negatively effect mRNA stability or expression.

The naturally-occurring encoding nucleotide sequence may already, in advance of any modification, contain a number of codons that correspond to a statistically-favored codon in a particular plant species. Therefore, codon optimization of the native nucleotide sequence may comprise determining which codons, within the native nucleotide sequence, are not statistically-favored with regards to a particular plant, and modifying these codons in accordance with a codon usage table of the particular plant to produce a codon optimized derivative. A modified nucleotide sequence may be fully or partially optimized for plant codon usage provided that the protein encoded by the modified nucleotide sequence is produced at a level higher than the protein encoded by the corresponding naturally occurring or native gene. Construction of synthetic genes by altering the codon usage is described in for example PCT Patent Application 93/07278.

Thus, the present invention encompasses nucleic acid sequences described hereinabove; fragments thereof, sequences hybridizable therewith, sequences homologous thereto, sequences orthologous thereto, sequences encoding similar polypeptides with different codon usage, altered sequences characterized by mutations, such as deletion, insertion or substitution of one or more nucleotides, either naturally occurring or man induced, either randomly or in a targeted fashion.

According to an embodiment of this aspect of the present invention the isolated polypeptide comprises an amino acid sequence as set forth by SEQ ID NO: 33.

The present invention also encompasses sequences homologous and orthologous to the above mentioned polypeptides, fragments of the above described polypeptides and polypeptides having mutations, such as deletions, insertions or substitutions of one or more amino acids, either naturally occurring or man induced, either randomly or in a targeted fashion.

Polynucleotides and polypeptides of the present invention are used for plant expression.

Expressing the exogenous polynucleotide of the present invention within the plant can be effected by transforming one or more cells of the plant with the exogenous polynucleotide, followed by generating a mature plant from the transformed cells and cultivating the mature plant under conditions suitable for expressing the exogenous polynucleotide within the mature plant.

Preferably, the transformation is effected by introducing to the plant cell a nucleic acid construct which includes the exogenous polynucleotide of the present invention and at least one promoter capable of directing transcription of the exogenous polynucleotide in the plant cell. Further details of suitable transformation approaches are provided hereinbelow.

As used herein, the term "promoter" refers to a region of DNA which lies upstream of the transcriptional initiation site of a gene to which RNA polymerase binds to initiate transcription of RNA. The promoter controls where (e.g., which portion of a plant, which organ within an animal, etc.) and/or when (e.g., which stage or condition in the lifetime of an organism) the gene is expressed.

Any suitable promoter sequence can be used by the nucleic acid construct of the present invention. Preferably the promoter is a constitutive promoter.

Suitable constitutive promoters include, for example, CaMV 35S promoter (SEQ ID NO: 46; Odell et al., Nature 313:810-812, 1985); Arabidopsis At6669 promoter (SEQ ID NO: 47); maize Ubi 1 (Christensen et al., Plant Sol. Biol. 18:675-689, 1992) (SEQ ID NO: 48); rice actin (McElroy et al., Plant Cell 2:163-171, 1990) (SEQ ID NO: 49); pEMU (Last et al., Theor. Appl. Genet. 81:581-588, 1991); and Synthetic Super MAS (Ni et al., The Plant Journal 7: 661-76, 1995) (SEQ ID NO: 50). Other constitutive promoters include those in U.S. Pat. Nos. 5,659,026, 5,608,149; 5.608,144; 5,604,121; 5.569,597: 5.466,785; 5,399,680; 5,268,463; and 5,608,142.

Suitable tissue-specific promoters include, but not limited to, leaf-specific promoters such as described, for example, by Yamamoto et al., Plant J. 12:255-265, 1997; Kwon et al., Plant Physiol. 105:357-67, 1994; Yamamoto et al., Plant Cell Physiol. 35:773-778, 1994; Gotor et al., Plant J. 3:509-18, 1993; Orozco et al., Plant Mol. Biol. 23:1129-1138, 1993; and Matsuoka et al., Proc. Natl. Acad. Sci. USA 90:9586-9590, 1993.

The nucleic acid construct of the present invention preferably further includes an appropriate selectable marker and/or an origin of replication. Preferably, the nucleic acid construct utilized is a shuttle vector, which can propagate both in *E. coli* (wherein the construct comprises an appropriate selectable marker and origin of replication) and be compatible for propagation in cells. The construct according to the present invention can be, for example, a plasmid, a bacmid, a phagemid, a cosmid, a phage, a virus or an artificial chromosome.

The nucleic acid construct of the present invention can be utilized to stably or transiently transform plant cells. In stable transformation, the exogenous polynucleotide of the present invention is integrated into the plant genome and as such it represents a stable and inherited trait. In transient transformation, the exogenous polynucleotide is expressed by the cell transformed but it is not integrated into the genome and as such it represents a transient trait.

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338:274-276).

The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) Direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledonous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

Preferably, mature transformed plants generated as described above are further selected for increase biomass, alcohol production, vigor and/or yield.

Although stable transformation is presently preferred, transient transformation of leaf cells, meristematic cells or the whole plant is also envisaged by the present invention.

Transient transformation can be effected by any of the direct DNA transfer methods described above or by viral infection using modified plant viruses.

Viruses that have been shown to be useful for the transformation of plant hosts include CAMV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Preferably, the virus of the present invention is avirulent and thus is incapable of causing severe symptoms such as reduced growth rate, mosaic, ring spots, leaf roll, yellowing, streaking, pox formation, tumor formation and pitting. A suitable avirulent virus may be a naturally occurring avirulent virus or an artificially attenuated virus. Virus attenuation may be effected by using methods well known in the art including, but not limited to, sub-lethal heating, chemical treatment or by directed mutagenesis techniques such as described, for example, by Kurihara and Watanabe (Molecular Plant Pathology 4:259-269, 2003), Gal-on et al. (1992), Atreya et al. (1992) and Huet et al. (1994).

Suitable virus strains can be obtained from available sources such as, for example, the American Type culture Collection (ATCC) or by isolation from infected plants. Isolation of viruses from infected plant tissues can be effected by techniques well known in the art such as described, for example by Foster and Tatlor, Eds. "Plant Virology Protocols: From Virus Isolation to Transgenic Resistance (Methods in Molecular Biology (Humana Pr), Vol 81)", Humana Press, 1998. Briefly, tissues of an infected plant believed to contain a high concentration of a suitable virus, preferably young leaves and flower petals, are ground in a buffer solution (e.g., phosphate buffer solution) to produce a virus infected sap which can be used in subsequent inoculations.

Construction of plant RNA viruses for the introduction and expression of non-viral exogenous polynucleotide sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; and Takamatsu et al. FEBS Letters (1990)269:73-76.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous polynucleotide sequences such as those included in the construct of the present invention is demonstrated by the above references as well as in U.S. Pat. No. 5,316,931.

In one embodiment, a plant viral polynucleotide is provided in which the native coat protein coding sequence has been deleted from a viral polynucleotide, a non-native plant viral coat protein coding sequence and a non-native promoter, preferably the subgenomic promoter of the non-native coat protein coding sequence, capable of expression in the plant host, packaging of the recombinant plant viral polynucleotide, and ensuring a systemic infection of the host by the recombinant plant viral polynucleotide, has been inserted. Alternatively, the coat protein gene may be inactivated by insertion of the non-native polynucleotide sequence within it, such that a protein is produced. The recombinant plant viral polynucleotide may contain one or more additional non-native subgenomic promoters. Each non-native subgenomic promoter is capable of transcribing or expressing adjacent genes or polynucleotide sequences in the plant host and incapable of recombination with each other and with native subgenomic promoters. Non-native (foreign) polynucleotide sequences may be inserted adjacent the native plant viral subgenomic promoter or the native and a non-native plant viral subgenomic promoters if more than one polynucleotide sequence is included. The non-native polynucleotide sequences are transcribed or expressed in the host plant under control of the subgenomic promoter to produce the desired products.

In a second embodiment, a recombinant plant viral polynucleotide is provided as in the first embodiment except that the native coat protein coding sequence is placed adjacent one of the non-native coat protein subgenomic promoters instead of a non-native coat protein coding sequence.

In a third embodiment, a recombinant plant viral polynucleotide is provided in which the native coat protein gene is adjacent its subgenomic promoter and one or more non-native subgenomic promoters have been inserted into the viral polynucleotide. The inserted non-native subgenomic promoters are capable of transcribing or expressing adjacent genes in a plant host and are incapable of recombination with each other and with native subgenomic promoters. Non-native polynucleotide sequences may be inserted adjacent the non-native subgenomic plant viral promoters such that the sequences are transcribed or expressed in the host plant under control of the subgenomic promoters to produce the desired product.

In a fourth embodiment, a recombinant plant viral polynucleotide is provided as in the third embodiment except that the native coat protein coding sequence is replaced by a non-native coat protein coding sequence.

The viral vectors are encapsidated by the coat proteins encoded by the recombinant plant viral polynucleotide to produce a recombinant plant virus. The recombinant plant viral polynucleotide or recombinant plant virus is used to infect appropriate host plants. The recombinant plant viral polynucleotide is capable of replication in the host, systemic spread in the host, and transcription or expression of foreign gene(s) (exogenous polynucleotide) in the host to produce the desired protein.

Techniques for inoculation of viruses to plants may be found in Foster and Taylor, eds. "Plant Virology Protocols: From Virus Isolation to Transgenic Resistance (Methods in Molecular Biology (Humana Pr), Vol 81)", Humana Press, 1998; Maramorosh and Koprowski, eds. "Methods in Virology" 7 vols, Academic Press, New York 1967-1984; Hill, S. A. "Methods in Plant Virology", Blackwell, Oxford, 1984; Walkey, D. G. A. "Applied Plant Virology", Wiley, N.Y., 1985; and Kado and Agrawa, eds. "Principles and Techniques in Plant Virology", Van Nostrand-Reinhold, N.Y.

In addition to the above, the polynucleotide of the present invention can also be introduced into a chloroplast genome thereby enabling chloroplast expression.

A technique for introducing exogenous polynucleotide sequences to the genome of the chloroplasts is known. This technique involves the following procedures. First, plant cells are chemically treated so as to reduce the number of chloroplasts per cell to about one. Then, the exogenous polynucleotide is introduced via particle bombardment into the cells with the aim of introducing at least one exogenous polynucleotide molecule into the chloroplasts. The exogenous polynucleotides selected such that it is integratable into the chloroplast's genome via homologous recombination which is readily effected by enzymes inherent to the chloroplast. To this end, the exogenous polynucleotide includes, in addition to a gene of interest, at least one polynucleotide stretch which is derived from the chloroplast's genome. In addition, the exogenous polynucleotide includes a selectable marker, which serves by sequential selection procedures to ascertain that all or substantially all of the copies of the chloroplast genomes following such selection will include the exogenous polynucleotide. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

Since increase in biomass in plants can involve multiple genes acting additively or in synergy (see, for example, in Quesda et al., Plant Physiol. 130:951-063, 2002), the present invention also envisages expressing a plurality of exogenous polynucleotides in a single host plant to thereby achieve enhanced biomass increases.

For example, the present invention contemplates co-expression of exogenous UGPase (EC 2.7.7.9). According to one embodiment the UGPase comprises an amino acid sequence at least 95% homologous, and/or at least 90% identical to SEQ ID NO: 35 as determined using the BlastP software of the National Center of Biotechnology Information (NCBI) using default parameters. Thus, for example the present invention contemplates expression of a polypeptide as set forth by SEQ ID NO: 35 by expression of a polynucleotide as set forth by SEQ ID NO: 36.

The nucleic acid sequence may be at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, or more say 100% identical to a nucleotide sequence selected from the sequence set forth by SEQ ID NO: 36.

Nucleic acid sequences may encode polypeptide sequences comprising an amino acid sequence at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, or more say 100% homologous to SEQ ID NO 35.

The present invention also contemplates co-expression of an exogenous uridyl transferase UT, (EC 2.7.7.12). According to one embodiment the UT comprises an amino acid sequence at least 85% homologous, and/or at least 75% identical to SEQ ID NO: 37 as determined using the BlastP software of the National Center of Biotechnology Information (NCBI) using default parameters. Thus, for example the present invention contemplates expression of a polypeptide as set forth by SEQ ID NO: 37 by expression of a polynucleotide as set forth by SEQ ID NO: 38.

The nucleic acid sequence may be at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, or more say 100% identical to a nucleotide sequence selected from the sequence set forth by SEQ ID NO: 38.

Nucleic acid sequences may encode polypeptide sequences comprising an amino acid sequence at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, or more say 100% homologous to SEQ ID NO 37.

Other polypeptides that may be co-expressed together with the UGPPases of the present invention include epimerases.

Expressing a plurality of exogenous polynucleotides in a single host plant can be effected by co-introducing multiple nucleic acid constructs, each including a different exogenous polynucleotide, into a single plant cell. The transformed cell can than be regenerated into a mature plant using the methods described hereinabove.

Alternatively, expressing a plurality of exogenous polynucleotides in a single host plant can be effected by co-introducing into a single plant-cell a single nucleic-acid construct including a plurality of different exogenous polynucleotides. Such a construct can be designed with a single promoter sequence which can transcribe a polycistronic message including all the different exogenous polynucleotide sequences. To enable co-translation of the different polypeptides encoded by the polycistronic message, the polynucleotide sequences can be inter-linked via an internal ribosome entry site (IRES) sequence which facilitates translation of polynucleotide sequences positioned downstream of the IRES sequence. In this case, a transcribed polycistronic RNA molecule encoding the different polypeptides described above will be translated from both the capped 5' end and the two internal IRES sequences of the polycistronic RNA molecule to thereby produce in the cell all the different polypeptides. Alternatively, the construct can include several promoter sequences each linked to a different exogenous polynucleotide sequence.

The plant cell transformed with the construct including a plurality of different exogenous polynucleotides, can be regenerated into a mature plant, using the methods described hereinabove.

Alternatively, expressing a plurality of exogenous polynucleotides in a single host plant can be effected by introducing different nucleic acid constructs, including different exogenous polynucleotides, into a plurality of plants. The regenerated transformed plants can then be cross-bred and resultant progeny selected for superior biomass traits, using conventional plant breeding techniques.

Hence, the present application provides methods of utilizing novel genes to increase biomass in a wide range of economical plants, safely and cost effectively.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Methods

1. Gene Cloning

UGGPase protein purification and peptide sequencing: Fresh tissue of melon fruitlets (*Cucumis melo*, subsp. melo Group Reticulatus, cv. Noy Yizre'el, 3 DAA, 3.5 g) was ground in liq N and protein was extracted with 20 ml of buffer containing 50 mM HEPES-NaOH (pH 7.5), 1 mM EDTA, 5 mM DTT, 1 mM PMSF, 0.1% PVP. After centrifugation at 10 000 g for 30 min the supernatant was filtered through 0.2 µm cellulose acetate filter (Schleicher & Schuell, Germany) and loaded on a MonoQ HR 5/5 (Pharmacia Biotech AB, Uppsala, Sweden) column as described in Petreikov et al. (2001). The column was equilibrated and the unbound protein washed out with 20 mM HEPES-NaOH (pH 7.2), 2.5 mM DTT (buffer A), and the bound protein was eluted with the 0-0.25 mM KCl gradient in the same buffer. Protein of the fractions exhibiting UDP-Gal/Glu PPase activity (described below) were concentrated by acetone precipitation and subjected to SDS-PAGE (10%), using a Bio-Rad Mini-Electrophoresis System according to the manufacturer's instruction. 40 µg and 10 µg of protein were loaded for Coomassie Brilliant Blue R-250 and immunoblotting, respectively. Polyclonal UDP-Gal PPase antibodies, developed as described by Feusi et al. [Feusi et al., (1999), Physiol Plant 106: 9-16] were used for immunoblotting at a dilution of 1:1000. Following immunoblotting, as described in Schaffer and Petreikov, (1997), Plant physiol 113: 739-746, the UDP-Gal/Glu PPase band was visualized using 5-bromo-4-chloro-3 indolyl phosphate/nitroblue tetrazolium (Promega, Madison Wis., USA), according to the manufacturer's instructions.

Peptide sequencing: The excised 68 kDa gel band stained with Coomassie Blue and corresponding to the band of UGGPase as determined by immunoblotting was subjected to MS/MS analysis following protein digestion treatment with trypsin, further mass spectrometry carried out with Qtof2 (Micromass, England) using nanospray attachment and data analysis (Qtof Laboratory Interdepartmental Equipment Unit, The Hebrew University Medical School, Israel). Seven peptide sequences were obtained and a BLAST analysis was carried out, identifying a homologous Arabidopsis gene At5g52560 of unknown function. Using the *Arabidopsis* protein sequence as a query, additional homologous genes were identified from the various plant EST data bases available at TIGR (www.tigr.org). The following ESTs were identified and used to perform a CLUSTAL W homology alignment to identify conserved sequences: wheat (TC251010), rice (TC277270), barley (TC148351).

UGGPase cloning: The initial DNA fragment of the melon UGGPase gene was cloned from young melon fruit cDNA using two degenerate primers: UGGP-F1 5'GCN GGN YTN AAR TGG GT3' (SEQ ID NO: 1) and UGGP-R1 5'GGC CAN ACY TCN ACY TC3', (SEQ ID NO: 2) based on the sequences AGLKWV (SEQ ID NO: 3) and EVEVWP (SEQ ID NO: 4). The 546 bp product was sequenced and cloning of the upstream region of the gene was carried out using the upstream degenerate primer UGGP-F3 5'TCN AGY TAY CCN GGN GG3' (SEQ ID NO: 5), for the SSYPGG (SEQ ID NO: 6), N-terminal sequence together with degenerate primer UGGP-R1 (SEQ ID NO: 2). The UGGPase full length sequence was cloned from a young melon fruit EST library (see below) using: (1) UGGPase internal primers: UGGP-R5' 5'CCCACCAGCAACAAGAACAAA3' (SEQ ID NO: 7) and UGGP-F3' 5'CTTCAACCCGATTGGAATGTA3' (SEQ ID NO: 8) and (2) primers of T7 and T3 promoter sequences from the multiple cloning site region of the pBK-CMV phagemid vector.

Young fruit EST library: Total RNA was isolated from 10 gr fresh weight from a mixture of 'Noy Yizre'el' fruits, collected at a 0, 1, 3, 12, and 25 DPA, using a modification of the method of La Claire and Herrin (1997), Plant Mol. Bio. Rep. 15: 263-272. Poly (A)$^+$ mRNA was purified from 1 mg of total RNA by use of Oligotex™ mRNA purification kit according to manufacturer's recommendations (Qiagen, Hilden, Germany). 5 µg of poly (A)$^+$ mRNA was used for preparation of the library. The EST library was constructed using ZAP cDNA Synthesis Kit and ZAP Express™ cDNA Gigapack™ III Gold Cloning Kit according to manufacturer's recommendations (Stratagene, La Jolla, Calif., U.S.A.). Phage clones were mass-excised to pBK-CMV phagemid vector following the manufacturer's instructions (Stratagene, La Jolla, Calif., U.S.A.).

UGPase cloning: Melon UGPase was cloned from young melon cDNA using four degenerate primers: UGP-F1 5'ACN ATG GGN TGY CAN GG3' (SEQ ID NO: 9); UGP-F2 5'GAY GGN TGG TAY CCN CC3' (SEQ ID NO: 10); UGP-R1, 5'CCN CCY TTN ACR TCN GC3' (SEQ ID NO: 11) and UGP-R2 5'CCR TCN ACY TCY TTN GG3' (SEQ ID NO: 12). The degenerate primers were constructed based on consensus amino acid sequences (TMGCTG (SEQ ID NO: 13), DGWYPP (SEQ ID NO: 14), ADVKGG (SEQ ID NO: 15), PKEVDG (SEQ ID NO: 16), respectively) identified by multiple alignments of potato (AAB71613), Arabidopsis (AKK64100), banana (AAF17422), rice (BAB69069), barley (CAA62689) and Japanese pear (BAA25917) published full length sequences. The initial 705 bp PCR fragment of the melon UGPase gene was cloned and sequenced using the T/A cloning vector pGEM-Teasy (Promega, Madison, Wis., USA). Melon UGPase full length sequence was cloned from a young melon (cv. Noy Yizre'el) cDNA library constructed in a yeast shuttle vector, pFL61 (Minet et al., 1992). The internal primers UGP-F202 5'ACATTCAACCAGAGC-CAATATC3' (SEQ ID NO: 17) and UGP-R603 5'CACCCA-CAAATTGTTAGTGTTG3' (SEQ ID NO: 18) together with the pFL61 flanking region primers pFL-F and pFL-R were used to clone the UGPase 5' and 3' regions and assemble the full gene sequence.

Uridyltransferase cloning: The cloning of melon Gal-1-P uridyltranferase (UT) gene from melon was also carried out based on conserved amino acid sequences. However, when this cloning work was started there were only a few partial plant ESTs in the databases, in addition to human, bacterial and fungal UTs and an Arabidopsis UT. Based on the CLUSTAL W homology alignment from plant UT sequences of tomato (TC103202), potato (TC41313), wheat (TC46973) and Arabidopsis (NM_121825) conserved sequences of E(H/Q)(E/Q)CAPE and QVFKN(Q/H)GA were selected for the preparation of degenerate primers. The first 320 bp of the melon Gal-1-P uridyltranferase (UT) gene was cloned by the degenerate primers: UT-F7 5'GAG CAN SAG TGY GCN CCN GAG3' (SEQ ID NO: 19) and UT-R7 5'GCN CCN TGG TTY TTG AAN ACC TG3' (SEQ ID NO: 20). Full sequence of the melon-UT was completed by direct sequencing of the BAC clone 121K16 selected from the CUGI (www.cugi.edu) melon BAC library MR-1 EcoR1 filters using the UT 320 bp fragment as a probe. Cloning was done from the BAC due to the very low abundance of UT mRNA in melon fruit. The primers: UT-R 5'ACATCCTCGGGGGTCAAATCAGA3' (SEQ ID NO: 21) and UT-F3'5'CAGGCTTCGGATTCAGACTTAG3' (SEQ ID NO: 22) were used to sequence the melon UT 5'end and 3'end from the BAC DNA, respectively.

2. Expression of UGPase, UGGPase and UT mRNA in *E. coli*.

Full length open reading frames were cloned in the bacterial expression vector pET-28a (Novagen, EMD Biosciences, San Diego, Calif., USA) using the following restriction sites: NdeI site for 5'end of the three ORFs; XhoI site for 3'end of the UGPase and UGGPase; and BamHI site for 3'end of UT.

Expression plasmids containing UGPase, UGGPase or UT mRNA were transformed into *E. coli* BL21 (DE3) LysE cells (Dubendorff and Studier, 1991). Bacterial colonies were grown in a 50-ml flask containing 10 ml of LB medium to an $OD_{600}$ of 0.5, induced for expression with 0.4 mM of IPTG, (control bacterial extracts were prepared from non-induced (−IPTG) cultures) and harvested after 6 hours or overnight by centrifugation at 4000 g for 10 min. Cells were lysed by re-suspension in 2 ml extraction buffer (20 mM phosphate buffer pH 8, 1 mM EDTA, 500 mM NaCl, 0.1% Triton ×100, 2.5 mm DTT and 1 mg/ml lysozyme) for 1 h at 4° C., and mechanically broken by freezing and thawing three times. The viscous bacterial lysate was sheared using a 21 gauge needle and crude soluble protein extract was obtained after centrifugation at 15,000 g for 30 min at 4° C. and collection of the soluble fraction. The bacterial crude proteins extracts were used to assay enzyme activities.

3. RNA Extraction Northern-Blot Analysis.

Total RNA was isolated from 10 gr fresh weight of melon flesh using a modification of the method of La Claire and Herrin (1997), Plant Mol. Bio. Rep. 15: 263-272. Each 10 gr sample was pooled from 3 melon fruit of the same developmental stage. For northern-blot analysis, 20 µg of total RNA from each developmental stage was separated on a denaturing 1% agarose-gel using Mops buffer. Expression of UGPase and UGGPase mRNAs were analyzed by RNA gel blotting using specific probes for UGPase (422 bp) and UGGPas (710 bp). Detection of UGPase and UGGPase mRNAs was analyzed using a Phospholmager (Molecular Dynamics, Sunnyvale, Calif.). To indicate the amount of RNA loaded in each well the nylon membrane was stained for 5 min with 5% methylene-blue.

4. Quantitative Real-Time PCR.

cDNA was synthesized from 1 µg RNA (DNase-treated) using the Reverse-iT™ 1$^{st}$ Strand Synthesis Kit (ABgene, Surrey, UK), according to manufacturer's instructions. 1 µl cDNA product was used as template for real-time PCR reaction based on Eurogentec qPCR™ core kit and SYBR$^R$ Green I as a fluorescent substance. The specific primers used for the UGGPase and UT genes were: UGGP-QF 5'AACCCGAT-TGGAATGTATGAT3' (SEQ ID NO: 23); UGGP-QR 5'CCGAAGTAGCACTGTGATAAG3' (SEQ ID NO: 24), and UT-QF 3'TCCTGCTCTCAGTAGGGATAAGG5 (SEQ ID NO: 25)'; UT-QR 5'ACATCCTCGGGGGTCAAAT-CAGA3' (SEQ ID NO: 26). The melon Actin cDNA (AY859055) was quantified with the following primers: forward, 5'GATTCCGTGCCCAGAAGTT3' (SEQ ID NO: 27) and reverse, 5'TTCCTTGCTCATCCTGTCTG3' (SEQ ID NO: 28) and used for normalizing the expression data. The real-time PCR reaction was initiated by heat activation of 10 min at 95° C. and continued for 40 cycles of 15 s at 95° C., 30 s at 60° C., and 30 s at 72° C., using the GeneAmp 5700 Sequence Detection System (PE Biosystems). Each specific amplicon: 167 bp for UGGPase, 159 bp for UT and 187 bp for the melon Actin genes had only one dissociation peak (not shown) and linear calibration curves (for all genes, $R^2$=0.96-0.99). The specific gene expression was calculated relative to the actin mRNA level in each sample according to the equation $2^{-Ct\ sample-Ct\ actin)}$, where Ct is the threshold cycle of the specific gene and actin.

5. Enzyme Extraction.

Assays of native fruit enzyme activities were carried out on the crude extracts as described in the enzyme purification section above. When enzyme fractions were separated by ion exchange chromatography, conditions were as described above with the exception of the separated tomato fruit extract in which the extraction buffer and elution buffer consisted of BisT Propane (pH 9.0) in an attempt to bind the UGPase enzyme to the MonoQ column.

Phenyl Sepharose Hydrophobic Interaction chromatography (Hi Trap HIC, 1 ml, Pharmacia Biotech) was also used for the separation of the melon UGGPase and UGPase enzymes. The extraction mixture consisted of 50 mM Phosphate (pH 7.0), 2 mM EDTA, 5 mM $MgCl_2$, 0.8 mM gal, 5 mM DTT, 1 mM PMSF. The supernatant after centrifugation at 10,000 g for 30 min was adjusted to 1M ammonium sulfate, incubated in ice for 20 min, centrifuged, filtered and applied in the column. The unbound protein washed out with 50 mM Phosphate (pH 7.0), 1 M ammonium sulfate and the bound protein was eluted with the 1-0 M ammonium sulfate gradient in the phosphate buffer.

The bacterial-expressed enzymes were extracted as described above. For ion exchange chromatographic separation the enzyme extracts were diluted in 25 mM HEPES-NaOH (pH 7.5), 1 mM EDTA, 5 mM $MgCl_2$, 0.5 mM DTT and separated by MonoQ anion-exchange chromatography under conditions identical to the melon fruit enzyme extract conditions described above.

6. Enzyme Assays.

Nucleotide-sugar synthesis direction: In the synthesis direction of UDP-sugars enzyme activities were assayed as described in detail by Gao et al. [Gao et al, (1999), Physiol Plant 106: 1-8; Gao et al, (1999), Plant Physiol 119: 979-988] using Glc-1-P or Gal-1-P as substrates. The reaction mixture, in a total volume of 0.2 ml, contained 25 mM HEPES-NaOH pH 7.5, 1 mM EDTA, 5 mM $MgCl_2$, 0.5 mM DTT, 10 mM Gal-1-P or Glc-1-P and 2.5 mM UTP. The reaction was initiated by adding 20 µl enzyme preparation at 30° C. and terminated after 3 min by 2 min boiling. After cooling to room temperature, 1 ml 50 mM Tricine buffer pH 8.7 containing 0.5 mM NAD, 0.01 unit of UDP-Glc dehydrogenase (Sigma) and 0.02 unit of UDP-Glc-4' epimerase (Sigma) was added and the mixture was incubated at 30° C. for 1 hr prior to measuring 340 nm. Enzyme activity was expressed as µmol UDP-Gal produced per min at 30° C.

For the determination of the kinetic parameters of the partially purified enzymes the substrates Glc-1-P and Gal-1-P were used in concentrations from 0 to 5 mM. The amount of UDP-sugars produced was quantified from standard curves of 0-75 nmol UDP-Glc and UDP-Gal in 0.5 ml of reaction mixture under the same assay conditions and activity was expressed as the production of µmol UDP-Glc or UDP-Gal per min at 30° C.

Pyrophosphorolytic direction: In the pyrophosphorolytic direction the sugar-phosphate production was measured according to Smart and Pharr (1981) Planta 153: 370-375, with modifications as follows. The reaction buffer contained 25 mM HEPES-NaOH (pH 7.5), 1 mM EDTA, 5 mM $MgCl_2$, 0.5 mM DTT with addition of 1 mM of either UDP-Glc or UDP-Gal and 10 µl of partially purified enzyme sample in a 100 µl reaction mixture. The reaction was initiated by 1 mM PPi and stopped after 3 min by boiling for 2 min and the mixture was cooled on ice. For the measurement of the respective hexose-1-P product a single mixture was added: 400 µl of 50 mM HEPES-NaOH pH (7.8) containing 5 mM $MgCl_2$, 4 mM UDPG, 0.02 U Gal-1-P Uridyltransferase (Sigma), 1 mM NAD, 10 µM gl-1,6 bis P, 2U Phosphoglucomutase (PGM) and 1 U Glc-6-P dehydrogenase (G6PDH, from *Leuconostoc*). After 40 min incubation at 30° C., absorbance of NADH product was recorded at 340 nm.

For the determination of kinetic parameters the substrates UDP-Glc or UDP-Gal were used in concentrations from 0 to 1 mM. The amount of hexose-P produced was quantified from a standard curve of 0-100 nmol Glc-1-P/Gal-1-P in 0.5 ml of reaction mixture under the same assay condition and expressed as µmol Glc-1-P/Gal-1-P per min at 30° C.

For screening enzyme activities in the HPLC fractions during purification two separate assays were used. For determining activity with the Glc moiety a coupled continuous assay was used in the pyrophosphorolytic direction and Glc-1-P formation was monitored as in Schaffer and Petreikov (1997), Plant physiol 113: 739-746. In brief, the PPi-dependent production of Glc-1-P from UDP-Glc was measured in a linked assay containing NADH, PGM and G6PDH. For the determination of fractions active with the Gal moiety we used the Gal-1-P specific assay described above in the nucleotide-sugar synthesis direction.

Gal-1-Phospate uridyltransferase (UT): Two separate methods were used to measure UT activity in light of the near absence of activity in melon fruit. A continuous coupled enzyme assay modified from Elsevier and Fridovich-Keil (1996), J Biol Chem 271: 32002-32007, was carried out in a 0.5 ml reaction mixture containing 50 mM HEPES-NaOH (pH 7.8), 5 mM $MgCl_2$, 0.5 mM DTT, 10 mM Gal-1-P, 1 mM NAD, 10 µM gl-1,6 bis P, 1 U G6PDH (from Leuconostoc), 2 U PGM, and enzyme sample. The reaction was initiated by 4 mM UDP-Glc and monitored for 10 min at 37° C. The amount of Glc-1-P produced was expressed as the amount of enzyme necessary to produce 1 µmol Glc-1-P per min at 37° C. Alternatively, a two-step end point assay, modified from Main et al. (1983), Physiol Plant 59: 387-392, was used for determining UT activity. The reaction buffer contained 25 mM HEPES-NaOH (pH 7.5), 1 mM EDTA, 5 mM $MgCl_2$, 0.5 mM DTT with addition of 10 mM Gal-1-P and 10 µl of partially purified enzyme sample in a 100 µl reaction mixture. The reaction was initiated by 4 mM UDP-Glc and stopped after 10 min by boiling for 2 min and the mixture was cooled on ice. For the measurement of the Glc-1-P product 400 µl consisting of 50 mM HEPES-NaOH pH (7.8) 5 mM $MgCl_2$, 1 mM NAD, 10 µM gl-1,6 bis P, 2 U PGM and 1 U G6PDH. After 40 min incubation at 30° C., absorbance of NADH product was recorded at 340 nm.

7. Protein Estimation

The Bio-Rad protein assay and BSA as a standard were used to estimate the protein concentration according to the method of Bradford et al. (1976), Anal Biochem 72: 248-254

Example 1

Purification and Peptide Sequencing and Cloning of UDP-Gal/Glc Pyrophosphorylase, UGPase and UT Results Antibodies prepared against the purified protein of Feusi et al [Feusi et al., 1999, Physiol Plant 106: 9-16] were used to identify a partially purified protein extract from young melon fruit (FIGS. 1A-C). The corresponding 68 kD band from the SDS-PAGE gel was excised and the protein sequenced after partial peptide hydrolysis.

Based on seven peptide sequences obtained (SEQ ID NOs: 39-45), a BLAST analysis was performed, identifying At5g52560 as a homologous gene (79%) included in Pfam01704 and containing a UGPase motif (FIG. 2A). Based on the homology with the Arabidopsis homologue and additional plant homologues reported in the TIGR EST databases, degenerate primers were synthesized and a 546 bp amplified product was sequenced. The upstream and downstream portions of the gene were sequenced from a young melon fruit cDNA library in pBK-CMV phagemid vector. FIG. 2A shows the deduced sequence of the protein and its homologies to similar plant enzymes, as well as the seven peptide sequences obtained. The calculated MW of the enzyme is 67,787 consistent with the band in FIGS. 1B-C. This enzyme is referred to as UDP-Gal/Glc pyrophosphorylase (UGGPase, deposited in gene bank as DQ399739).

The genes for melon fruit UGPase and UT were cloned by PCR, based on homologous and conserved sequences of other plant genes in the database (as indicated in FIGS. 2B-C). Full length sequences were obtained from the young fruit cDNA library and melon BAC library for UGPase and UT, respectively. The UGPase gene encodes for a protein of 52 kDa and the UT gene encodes for a protein of 38 kD, consistent with the MW of enzymes in these two families.

Example 2

Functional Expression and Characterization of the Gene Products

Results

FIGS. 3A-C show the heterologously expressed proteins of UGGPase, UGPase, and UT in *E. coli* extracts. The expressed UGGPase, UGPase, enzymes were active and were partially purified by ion exchange chromatography and characterized with regard to substrate specificity and affinity. The UT enzyme was sequestered in inclusion bodies. Mass spectrometry analysis of the differentially expressed band in FIG. 3C indicated that it is indeed UT (results not shown).

The novel UGGPase can utilize both Glc-1-P and Gal-1-P in the synthesis of the respective nucleotide sugars and also can utilize either UDP-Glc or UDP-Gal in the reverse direction. Substrate affinity is higher for the Glc moiety in both directions but $V_{max}$ is higher for the Gal moiety in each direction as illustrated in Table 1, herein below.

TABLE 1

Km (mM) and Vmax (μmol mg protein$^{-1}$ min$^{-1}$) of heterologously expressed and partially purified melon UGGPase and UGPase.

| | pyrophosphorolysis | | | | UDP sugar synthesis | | | |
|---|---|---|---|---|---|---|---|---|
| | UDP-Gal | | UDP-Glc | | Gal-1-P | | Glc-1-P | |
| Enzyme | Km | Vmax | Km | Vmax | Km | Vmax | Km | Vmax |
| UGGPase | 0.44 | 625 | 0.14 | 238 | 0.43 | 714 | 0.27 | 222 |
| UGPase | 0.26 | 714 | 0.11 | 277 | ND | ND | 0.24 | 238 |

ND, Not detected.

The heterologously expressed melon UGPase is specific for the Glc moiety in the direction of nucleotide sugar synthesis (using Glc-1-P as substrate) and shows no observable activity with Gal-1-P. However, in the reverse direction, the UGPase did show activity with UDP-Gal, as well as with UDP-Glc. Affinity of the UGPase for the UDP-Gal is slightly lower than for UDP-Glc; however, the $V_{max}$ is significantly higher In light of the surprising result that the melon UGPase is active with UDP-Gal, the characteristics of the purified melon UGPase were compared with those from a non-cucurbit plant, young tomato fruit, in order to determine whether the ability to metabolize UDP-Gal is unique to the melon UGPase. Surprisingly, it was observed that a partially purified tomato fruit UGPase did, in fact, metabolize UDP-Gal in addition to UDP-Glc as illustrated in Table 2 herein below.

TABLE 2

Comparison of substrate specificity of melon and tomato UGPase and UGGPase. Control non-induced transformed *E. coli* extracts (−IPTG) showed ca 5% of the activity with either UDP-Gal and UDP-Glc, as compared to the induced (+IPTG) *E. coli* extracts.

| | Enzyme activity, μmol mg protein$^{-1}$ min$^{-1}$ | | |
|---|---|---|---|
| Substrates | melon UGPase *E. coli* | melon UGGPase *E. coli* | tomato UGPase native |
| UDP-Gal + PPi | 460 | 410 | 12 |
| UDP-Glc + PPi | 245 | 233 | 38 |
| Gal-1-P + UTP | ND | 678 | ND |
| Glc-1-P + UTP | 187 | 223 | 8 |

ND, Not detected.

The tomato enzyme fraction did not show any UDP-Glc-4' epimerase activity (not shown), indicating that the activity measured with UDP-Gal was not an artifact due to UDP-Gal to UDP-Glc conversion. In the reverse direction the tomato UGPase was specific for Glc-1-P and did not metabolize Gal-1-P, similar to the melon UGPase and indicating that the partially purified fraction did not contain a UGGPase.

Example 3

Gal Metabolism Gene Expression and Enzyme Activities in Young Fruit

Results

In order to determine the potential relative contribution of the three enzymes in Gal-1-P flux in developing melon fruit, crude extracts were assayed from immature and developing ovaries and compared to the relative quantitative expression of their respective genes. The enzyme activities of the UGPase, UGGPase and UT in developing ovaries are presented in Table 3 herein below.

TABLE 3

Activity of UGGPase, UGPase and UT in crude extracts from young melon ovaries

| Substrate | Assay for enzyme | Activity (µmol product mg protein$^{-1}$ min$^{-1}$) |
|---|---|---|
| Gal-1-P + UTP | UGGPase | 8 |
| UDP-Glc + PPi | UGPase + UGGPase | 14 |
| UDP-Glc + Gal-1-P | UT | 0.007 |

Figure 4:
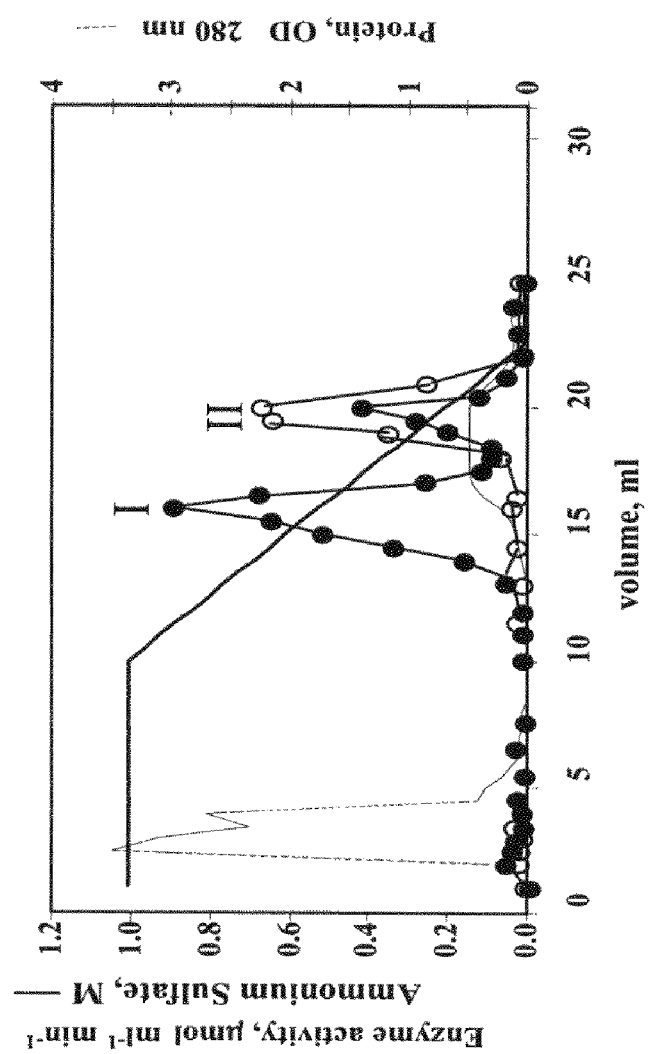
FIG. 4 is a graph depicting hydrophobic interaction chromatography separation (HIC, phenyl sepharose) of UGPase (SEQ ID NO: 35) and UGGPase (SEQ ID NO: 33) from melon fruit ovaries. Closed circles indicate activity with Gal-1-P and open circles indicate activity with Glc-1-P. Peak I is the Glc-1-P specific UGPase and peak II is the UGGPase enzyme.

The assay of UGGPase was carried out using Gal-1-P as substrate so that the assay was specific for this enzyme. However, since both UGPase and UGGPase are active with the Glc moiety in either direction the assay does not distinguish between the two enzymes. The two activities were therefore separated using hydrophobic interaction chromatography and the results show that the two enzymes are of approximate equal activity (FIG. 4). The results indicate that Gal-1-P metabolism is carried out preferentially by the UGGPase enzyme. Although both the UGGPase as well as the Glc-1-P specific UGPase are active in the developing fruit, the latter is inactive on the galactokinase reaction product Gal-1-P, as described above. UT activity is barely observed in the developing ovaries (Table 3).

The gene expression patterns of the three genes paralleled the enzyme activity in crude extracts of developing melon ovaries and fruit. Northern blots showed expression of both UGGPase and UGPase throughout fruit development while UT expression was not observed at the level of detection of Northern blots (FIG. 5A). Quantitative RT-PCR was performed on mRNA of melon ovaries and developing fruit and UT expression was very low, compared to UGGPase (FIG. 5B).

Example 4

Flux of Gal-1-P

Results

In order to prove that both pyrophosphorylase reactions in the Gal-1-P to Glc-1-P flux can be carried out in consort by UGGPase in the absence of UGPase, Glc-1-P production was measured from the substrates Gal-1-P and UTP in the presence of only UGGPase and epimerase. PPi was also not added in order to test whether the second pyrophosphorylase reaction which is dependent on PPi can take place dependent on the production of PPi in the initial reaction. The partially purified native melon UGGPase (Table 4, herein below), as well as the heterologously expressed melon UGGPase (Table 5, herein below), were each used in conjunction with a purified epimerase to make certain that UGPase activity was not present. The Glc-1-P product was continuously removed by the linked PGM and G6PDH reactions in an enzyme-linked assay. The results of these experiments (as set forth in Tables 4 and 5, herein below) show that the UGGPase alone can carry out both the Gal-1-P conversion to UDP-Gal and the subsequent reverse reaction of UDP-Glc to Glc-1-P. Most significantly, the synthesis of Glc-1-P from UDP-Glc took place without the external addition of PPi, indicating that the PPi produced in the Gal-1-P+UTP→UDP-Gal+PPi reaction was cycled into the reverse reaction following the epimerase step.

TABLE 4

Dependence of Glc-1-P production from Gal-1-P and UTP on the addition of partially purified melon fruit UGGPase and purified epimerase. Each reaction was carried out with ca 13 µg protein from fraction 18 of FIG. 1a in a 1 ml reaction mix.

| | Enzyme in reaction | | Glc-1-P produced (µmol |
|---|---|---|---|
| Substrate | UGGPase | epimerase | Glc-1-P mg protein$^{-1}$ min$^{-1}$) |
| Gal-1-P, UTP | + | + | 1.8 |
| Gal-1-P, UTP | + | − | ND |
| Gal-1-P, UTP | − | − | ND |

ND, no activity detected

TABLE 5

Glc-1-P production from Gal-1-P and UTP with crude extracts of E. coli expressed protein of either melon UGGPase or melon UGPase, together with purified epimerase. The E. coli extract (−IPTG) did not express the UGGPase protein and served as blank reaction. Each reaction was carried out with ca 10 µg protein from the crude E. coli extractions shown in FIG. 3 in a 1 ml reaction mix.

| Substrate | E. coli extract | Glc-1-P produced (µmol Glc-1-P mg protein$^{-1}$ min$^{-1}$) |
|---|---|---|
| Gal-1-P, UTP | UGGPase, −IPTG | ND |
| Gal-1-P, UTP | UGGPase, +IPTG | 14.5 |
| Gal-1-P, UTP | UGPase, +IPTG | ND |

ND, no activity detected.

Example 6

Tobacco Transformation with UGGPPase

Materials and Methods

Cloning of UGGPPase and plasmid construction for tobaco transformation: UGGPPase was cloned from fresh melon fruitlets as described above, and inserted into the pGA643 binary vector (Genbank AY804024) with the cauliflower mosaic virus 35S constitutive promoter (Benfey and Chua, 1990 Benfey, P. N. and Chua, N.-H. (1990) The cauliflower mosaic virus 35S promoter: combinatorial regulation of transcription in plants. Science, 250, 959-966). This plasmid also contained the nptII gene under the control of Nopalin synthase (nos) promoter and terminator.

Plant Transformation and Maintenance

*Nicotiana tabacum* cv. Xanthi NN (tobacco) was transformed using *Agrobacterium tumefaciens* strain EHA105 (Hood et al., 1993 Transgenic Res. 2, 208-218) employing a standard leaf disc inoculation method. Binary plasmids were inserted into EHA105 via electroporation and plated on LB-Agar medium with 50 mg/l kanamycin. Tobacco Leaf discs were cut and plated abaxially on Petri-dish containing $D_0$ medium (Full MS (Murashige and Skoog)+3% sucrose supplemented with 0.1 mg/ml of a-naphthalene acetic acid (NAA) and 1 mg/ml 6-benzylaminopurine (BA), and solidified with 0.8% (w/v) plant-agar (Duchefa)). After 24 hours of pre-cultivation, the leaf explants were floated with logarithmic culture (OD~0.3) of the transformant EHA105 supplemented with Acetosyringone (100 µM final concentration) and incubated for 1 hour at room temperature. After 1 hour, the remaining bacterial suspension was pumped out and the leaf discs were co-cultivated for 48 hours in the dark. The explants were then transferred to selective regeneration medium $D_1$ (MS minerals with 400 mg/L carbenicillin, 70 mg/L kanamycin, 0.1 mg/L NAA and 1 mg/L BA). Regenerated explants were transferred to fresh medium biweekly. Green shoots, 1-3 cm tall, were separated from calli and transferred to Rooting medium containing full MS minirals, 200 mg/L carbenicillin, 75 mg/L kanamycin and 1 mg/L Indole butyric acid (IBA). Rooted plants were transplanted to peat cookies (Jiffy 7) for hardening and then grown in 4 liter pots in the greenhouse.

Plants were confirmed as transgenic by PCR screening of genomic DNA employing the nptII specific primers: NPT-F 5'CACGCAGGTTCTCCGGCCGC 3' (SEQ ID NO: 29) and NPT-R 5'TGCGCTGCGAATCGGGAGCG 3' (SEQ ID NO: 30) and gene-specific oligonucleotides: GaIPP-F 5' CAG-CAATAGACTGGCAGGTGA 3' (SEQ ID NO: 31) and GaIPP-R 5' CCAATCGGGTTGAAGACTTGA 3' (SEQ ID NO: 32). Genomic DNA was isolated using the DNeasy Plant Mini Kit (Qiagen, Mississauga, Ontario).

Plant growth: Primary transformed plants and control lines ($T_0$) were grown to maturity and self-fed to generate $T_1$ lines of all the single transformants and the associated controls. The pods were collected, and the seeds removed and sterilized by washing for 2 min in a 10% bleach solution, followed by a 1-min rinse in sterile water. Seeds were germinated on solid half-strength MS medium with % sucrose and kanamycin (50 mg/L). The surviving seedlings were then PCR screened using the aforementioned primer sets. Seedlings were grown in GA-7 vessels prior to transfer into 7.5-L pots containing a 50% peat-25% fine bark-25% pumice soil mixture in the glasshouse, and covered with 16-oz clear plastic cups for 1 week to aid in acclimation. Each line, transgenic and control, was represented by 12 individual plants (each from an individually selected seed). 15 Transcription levels: Semi quantitative RT-PCR was used to determine the transcript level of each transgene. Leaf sections weighing approximately 100 mg were ground in liquid nitrogen, and RNA was extracted using EZ-RNA total RNA extraction kit reagent (Biological Industries, Bet Haemek, Israel), according to the manufacturer's instructions. Following extraction, 20 µg of total RNA was treated 20 with 2 unit of DNase I (Fermentas) according to the manufacturer's instructions. The reaction was incubated at 37° C. for 30 min and then heat inactivated at 80° C. for 10 min.

Equal quantities of total RNA (2 µg) were employed for the synthesis of cDNA using RevertAid Hminus M-Mulv Reverse Transcriptase (Fermentas) and oligo $dT_{12-18}$ primer, and random hexamers, according to the manufacturer's instructions. PCR was carried out at Tm temperature of 62° C. using 1 µl of the first-strand cDNA product of the above reaction as a templates and UGGPase specific primers GaIPP-F and GaIPP-R (see above). Reactions were run for both 25 and 35 cycles so that the results can be interpreted in semi-quantitative manner. PCR reaction products were run on 1% agarose gels, stained and photographed. The results of 25 cycles show that the expression levels of the UGGPPase gene varied between the independent transformants (FIG. 8). Highest expression was observed in UGGP4, 10, 11 and 23. UGGP19 and UGGP21 were non-transformed individuals.

Enzyme activity of transgenic tobacco plants: Leaf samples (approximately 400 mg fresh weight) were ground in liquid N and protein was extracted with 1 ml of buffer containing 50 mM HEPES-NaOH (pH 7.5), 1 mM EDTA, 5 mM DTT, 1 mM PMSF, 2% PVPP. After centrifugation at 10 000 g for 30 min the supernatant was used as the crude enzyme extract. UGGPPase was assayed in the nucleotide-sugar synthesis direction using gal-1-P as substrate, as described above. In brief, the reaction mixture, in a total volume of 0.1 ml, contained 25 mM HEPES-NaOH pH 7.5, 1 mM EDTA, 5 mM $MgCl_2$, 0.5 mM DTT, 10 mM Gal-1-P and 2.5 mM UTP. The reaction was initiated by adding 10 µl enzyme preparation at 30° C. and terminated after 3 min by 2 min boiling. After cooling to room temperature, 0.4 ml 50 mM Tricine buffer pH 8.7 containing 0.5 mM NAD, 0.01 unit of UDP-Glc dehydrogenase (Sigma) and 0.02 unit of UDP-Glc-4' epimerase (Sigma) was added and the mixture was incubated at 30° C. for 1 hr prior to measuring 340 nm. Enzyme activity was expressed as µmol UDP-Gal produced per min at 30° C.

Plant growth: The glasshouse plants were harvested at the onset of flowering, as indicated by the formation of flower buds. The plant height, from base to tip of the highest bud, was measured prior to harvest. The developmental stages of tissues were standardized by employing a plastichron index (PI) (PI=0 was defined as the first leaf greater than 5 cm in length; PI=1 was the leaf immediately below PI=0). A portion of the stem from each plant spanning PI=5 to PI=15 was excised and immediately weighed for total stem fresh weight measurements and leaf biomass. This same section was then dried at 105° C. for 48 h for dry weight determination, and retained for further analysis. The internode distance represents the average length between each internode spanning PI=5 to PI=15. The lower section of the stem (below PI=15) was dried at room temperature for fibre quality analysis. Data is analyzed for growth rate on fresh and dry weight bases.

Soluble carbohydrate and starch analysis: Soluble carbohydrates (glucose, fructose and sucrose) are extracted from plant material (leaf, stem, roots) using five successive extractions in hot (68° C.) ethanol: $H_2O$ (80:20). The ethanol is evaporated and the dried residue is suspended in double distilled $H_2O$, centrifuged to remove debris and filtered through a 45 micron filter. Sugars are separated chromatographically by HPLC (Shimadzu LC10AT) in a Bio-Rad Fast Carbohydrate column according to the manufacturer's directions (Bio-Rad Laboratories, Hercules, Calif., USA). Sucrose, glucose and fructose are identified refractometrically (Shimadzu RID) by their retention time and quantified by comparison with sugar standards.

The remaining pellet after the hot (68° C.) ethanol: $H_2O$ extraction is assayed for starch following an overnight amyloglucosidase treatment and assay of released glucose using the dinitrosalicylic reagent, as described in Schaffer et al., 1987, Phytochemistry 26:1883-1887.

Determination of cellulose and holocellulose content: Dried plant stem material is ground using a Wiley mill to pass through a 30-mesh screen, and then Soxhlet-extracted with acetone for 24 h. The extractive free material is used for all further analyses. Holocellulose and a-cellulose is determined using a modified microanalytical method developed by Yokoyama et al. (2002), J Agric Fd Chem 50:, 1040-1044. In short, 200 mg of ground sample is weighed into a 25-mL round-bottomed flask and placed in a 90° C. oil bath. The reaction is initiated by the addition of 1 mL of sodium chlorite solution (400 mg 80% sodium chlorite, 4 mL distilled water, 0.4 mL acetic acid). An additional 1 mL of sodium chlorite solution is added every half hour and the sample removed to a cold water bath after 2 h. The sample is filtered through a coarse crucible, dried overnight and the holocellulose composition determined gravimetrically. Fifty milligrams of this dried holocellulose sample is weighed into a reaction flask and allowed to equilibrate for 30 min. Four millilitres of 17.5% sodium hydroxide are added and allowed to react for 30 min, after which 4 mL of distilled water is added. The sample is macerated for 1 min, allowed to react for an additional 29 min and then filtered through a coarse filter. Following a 5-min soak in 1.0 M acetic acid, the sample is washed with 90 mL of distilled water and dried overnight. The α-cellulose content is then determined gravimetrically.

Results

Results show that enzyme activity was more than doubled in some of the transformants, as compared to the non-transformed control. The results comparing the semi-quantitative expression in FIG. 8 and the enzyme activity in Table 6 show that there is a good correlation between the gene expression levels and enzyme activity. Both gene expression as well as enzyme activity were highest in lines 4, 10, 11, 23.

TABLE 6

Enzyme activity in transformed tobacco plants harboring the UGGPPase gene. Each plant is from an independent transgenic event. Basal enzyme activity of the non-transformed tobacco plants is listed as NN.

| Tobacco line | Enzyme activity (UDPgalactose formed per min per gfw) |
|---|---|
| NN1 | 6.8 |
| NN2 | 6.5 |
| UGGP4 | 10.6 |
| UGGP6 | 4.0 |
| UGGP10 | 14.8 |
| UGGP11 | 14.5 |
| UGGP19 | 2.4 |
| UGGP21 | 7.1 |
| UGGP23 | 13.0 |
| UGGP29 | 12.3 |
| UGGP37 | 7.1 |

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An isolated polynucleotide comprising a nucleic acid sequence encoding the polypeptide as set forth in SEQ ID NO: 33.

2. An isolated polynucleotide comprising the nucleic acid sequence as set forth in SEQ ID NO: 34.

3. A plant cell comprising an exogenous polypeptide as set forth in SEQ ID NO: 33.

4. The plant cell of claim 3, wherein said plant cell forms a part of a plant.

5. The plant cell of claim 3, further comprising an exogenous UGPase.

6. The plant cell of claim 5, wherein said exogenous UGpase comprises the amino acid sequence as set forth in SEQ ID NO: 35.

7. A method of increasing biomass, vigor and/or yield of a plant comprising expressing within the plant the exogenous polypeptide as set forth in SEQ ID NO: 33, thereby increasing biomass, vigor and/or yield of the plant.

8. The method of claim 7, wherein said expressing is effected by introducing to said plant a nucleic acid construct which comprises a polynucleotide sequence encoding said polypeptide and at least one promoter capable of directing transcription of said polynucleotide in said plant.

9. The method of claim 8, wherein said at least one promoter is a constitutive promoter.

10. The method of claim 8, wherein said at least one promoter is an inducible promoter.

11. The method of claim 8, wherein said expressing is effected by infecting said plant with a virus.

12. The method of claim 11, wherein said virus is an avirulent virus.

13. The method of claim 7, further comprising expressing within the plant an exogenous UGPase.

* * * * *

SEQUENCE LISTING

```
<160> NUMBER OF SEQ ID NOS: 50

<210> SEQ ID NO 1
<211> LENGTH: 17
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 1
gcnggnytna artgggt                                                  17

<210> SEQ ID NO 2
<211> LENGTH: 17
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
```

-continued

```
<400> SEQUENCE: 2
ggccanacyt cnacytc                                                    17

<210> SEQ ID NO 3
<211> LENGTH: 6
<212> TYPE: PRT
<213> ORGANISM: Artificial sequence
<220> FEATURE:
<223> OTHER INFORMATION: Melon UGGPase conserved peptide used for
      preparation of a degenerate primer

<400> SEQUENCE: 3

Ala Gly Leu Lys Trp Val
1               5

<210> SEQ ID NO 4
<211> LENGTH: 6
<212> TYPE: PRT
<213> ORGANISM: Artificial sequence
<220> FEATURE:
<223> OTHER INFORMATION: Melon UGGPase conserved peptide used for
      preparation of a degenerate primer

<400> SEQUENCE: 4

Glu Val Glu Val Trp Pro
1               5

<210> SEQ ID NO 5
<211> LENGTH: 17
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 5
tcnagytayc cnggngg                                                    17

<210> SEQ ID NO 6
<211> LENGTH: 6
<212> TYPE: PRT
<213> ORGANISM: Artificial sequence
<220> FEATURE:
<223> OTHER INFORMATION: Melon UGGPase conserved peptide used for
      preparation of a degenerate primer

<400> SEQUENCE: 6

Ser Ser Tyr Pro Gly Gly
1               5

<210> SEQ ID NO 7
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 7
```

-continued cccaccagca acaagaacaa a                                              21

<210> SEQ ID NO 8
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 8
cttcaacccg attggaatgt a                                              21

<210> SEQ ID NO 9
<211> LENGTH: 17
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 9
acnatgggnt gycangg                                                   17

<210> SEQ ID NO 10
<211> LENGTH: 17
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 10
gayggntggt ayccncc                                                   17

<210> SEQ ID NO 11
<211> LENGTH: 17
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 11
ccnccyttna crtcngc                                                    17

<210> SEQ ID NO 12
<211> LENGTH: 17
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 12
ccrtcnacyt cyttngg                                                    17

<210> SEQ ID NO 13
<211> LENGTH: 6
<212> TYPE: PRT
<213> ORGANISM: Artificial sequence
<220> FEATURE:
<223> OTHER INFORMATION: UGPase consensus amino acid sequences

<400> SEQUENCE: 13

Thr Met Gly Cys Thr Gly
1               5

<210> SEQ ID NO 14
<211> LENGTH: 6
<212> TYPE: PRT
<213> ORGANISM: Artificial sequence
<220> FEATURE:
<223> OTHER INFORMATION: UGPase consensus amino acid sequences

<400> SEQUENCE: 14

Asp Gly Trp Tyr Pro Pro
1               5

<210> SEQ ID NO 15
<211> LENGTH: 6
<212> TYPE: PRT
<213> ORGANISM: Artificial sequence
<220> FEATURE:
<223> OTHER INFORMATION: UGPase consensus amino acid sequences

<400> SEQUENCE: 15

Ala Asp Val Lys Gly Gly
1               5

<210> SEQ ID NO 16
<211> LENGTH: 6
<212> TYPE: PRT
<213> ORGANISM: Artificial sequence
<220> FEATURE:
<223> OTHER INFORMATION: UGPase consensus amino acid sequences

<400> SEQUENCE: 16

Pro Lys Glu Val Asp Gly
1               5

<210> SEQ ID NO 17
<211> LENGTH: 22
<212> TYPE: DNA
<213> ORGANISM: Artificial sequence
<220> FEATURE:

<223> OTHER INFORMATION: Single strand DNA oligonucleotide

<400> SEQUENCE: 17
acattcaacc agagccaata tc                                             22

<210> SEQ ID NO 18
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 18
cacccacaaa ttgttagtgt tg                                             22

<210> SEQ ID NO 19
<211> LENGTH: 21
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 19
gagcansagt gygcnccnga g                                              21

<210> SEQ ID NO 20
<211> LENGTH: 23
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 20
gcnccntggt tyttgaanac ctg                                            23

<210> SEQ ID NO 21
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 21
acatcctcgg gggtcaaatc aga                                            23

<210> SEQ ID NO 22

```
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 22
caggcttcgg attcagactt ag                                              22

<210> SEQ ID NO 23
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 23
aacccgattg gaatgtatga t                                               21

<210> SEQ ID NO 24
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 24
ccgaagtagc actgtgataa g                                               21

<210> SEQ ID NO 25
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 25
tcctgctctc agtagggata agg                                             23

<210> SEQ ID NO 26
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 26
acatcctcgg gggtcaaatc aga                                             23

<210> SEQ ID NO 27
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 27
gattccgtgc ccagaagtt                                                  19

<210> SEQ ID NO 28
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 28
```

```
ttccttgctc atcctgtctg                                              20
```

<210> SEQ ID NO 29
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 29

```
cacgcaggtt ctccggccgc                                              20
```

<210> SEQ ID NO 30
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 30

```
tgcgctgcga atcgggagcg                                              20
```

<210> SEQ ID NO 31
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 31

```
cagcaataga ctggcaggtg a                                            21
```

<210> SEQ ID NO 32
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 32

```
ccaatcgggt tgaagacttg a                                            21
```

<210> SEQ ID NO 33
<211> LENGTH: 614
<212> TYPE: PRT
<213> ORGANISM: Cucumis melo

<400> SEQUENCE: 33

```
Met Ala Ser Ser Leu Asp Ser Ala Ala Leu Thr Leu Ser Asn Leu Ser
1               5                   10                  15

Ile Asn Gly Asp Phe Ala Ser Ser Leu Pro Asn Leu Gln Lys Asn Leu
            20                  25                  30

His Leu Leu Ser Pro Gln Gln Val Glu Leu Ala Lys Ile Leu Leu Glu
        35                  40                  45

Leu Gly Gln Ser His Leu Phe Glu His Trp Ala Glu Pro Gly Val Asp
    50                  55                  60

Asp Asn Glu Lys Lys Ala Phe Phe Asp Gln Val Ala Arg Leu Asn Ser
65                  70                  75                  80

Ser Tyr Pro Gly Gly Leu Ala Ser Tyr Ile Lys Thr Ala Arg Gly Leu
                85                  90                  95

Leu Ala Asp Ser Lys Glu Gly Lys Asn Pro Phe Asp Gly Phe Thr Pro
            100                 105                 110

Ser Val Pro Thr Gly Glu Val Leu Thr Phe Gly Asp Asp Ser Phe Val
```

-continued

```
              115                 120                 125
Ser Phe Glu Asp Arg Gly Val Arg Glu Ala Arg Lys Ala Ala Phe Val
130                 135                 140
Leu Val Ala Gly Gly Leu Gly Glu Arg Leu Gly Tyr Asn Gly Ile Lys
145                 150                 155                 160
Val Ala Leu Pro Ala Glu Thr Thr Thr Gly Thr Cys Phe Leu Gln Ser
                165                 170                 175
Tyr Ile Glu Tyr Val Leu Ala Leu Arg Glu Ala Ser Asn Arg Leu Ala
                180                 185                 190
Gly Glu Ser Glu Thr Glu Ile Pro Phe Val Ile Met Thr Ser Asp Asp
            195                 200                 205
Thr His Thr Arg Thr Val Glu Leu Leu Glu Ser Asn Ser Tyr Phe Gly
        210                 215                 220
Met Lys Pro Ser Gln Val Lys Leu Leu Lys Gln Glu Lys Val Ala Cys
225                 230                 235                 240
Leu Asp Asp Asn Glu Ala Arg Leu Ala Val Asp Pro His Asn Lys Tyr
                245                 250                 255
Arg Ile Gln Thr Lys Pro His Gly His Gly Asp Val His Ala Leu Leu
                260                 265                 270
Tyr Ser Ser Gly Leu Leu Lys Asn Trp His Asn Ala Gly Leu Arg Trp
            275                 280                 285
Val Leu Phe Phe Gln Asp Thr Asn Gly Leu Leu Phe Lys Ala Ile Pro
        290                 295                 300
Ala Ser Leu Gly Val Ser Ala Thr Arg Glu Tyr His Val Asn Ser Leu
305                 310                 315                 320
Ala Val Pro Arg Lys Ala Lys Glu Ala Ile Gly Gly Ile Thr Arg Leu
                325                 330                 335
Thr His Thr Asp Gly Arg Ser Met Val Ile Asn Val Glu Tyr Asn Gln
                340                 345                 350
Leu Asp Pro Leu Leu Arg Ala Thr Gly Phe Pro Asp Gly Asp Val Asn
            355                 360                 365
Asn Glu Thr Gly Tyr Ser Pro Phe Pro Gly Asn Ile Asn Gln Leu Ile
        370                 375                 380
Leu Glu Leu Gly Ser Tyr Ile Glu Glu Leu Ser Lys Thr Gln Gly Ala
385                 390                 395                 400
Ile Lys Glu Phe Val Asn Pro Lys Tyr Lys Asp Ala Thr Lys Thr Ser
                405                 410                 415
Phe Lys Ser Ser Thr Arg Leu Glu Cys Met Met Gln Ser Tyr Pro Lys
                420                 425                 430
Thr Leu Pro Pro Ser Ala Arg Val Gly Phe Thr Val Met Asp Thr Trp
            435                 440                 445
Val Ala Tyr Ala Pro Val Lys Asn Asn Pro Glu Asp Ala Ala Lys Val
        450                 455                 460
Pro Lys Gly Asn Pro Tyr His Ser Ala Thr Ser Gly Glu Met Ala Ile
465                 470                 475                 480
Tyr Arg Ala Asn Ser Leu Val Leu Arg Lys Ala Gly Val Lys Val Ala
                485                 490                 495
Asp Pro Val Glu Gln Val Phe Asn Gly Gln Glu Val Glu Val Trp Pro
            500                 505                 510
Arg Ile Thr Trp Lys Pro Lys Trp Gly Leu Thr Phe Ser Glu Ile Lys
        515                 520                 525
Ser Lys Ile Asn Gly Asn Cys Ser Ile Ser Pro Arg Ser Thr Leu Val
530                 535                 540
```

```
Ile Lys Gly Lys Asn Val Tyr Leu Lys Asp Leu Ser Leu Asp Gly Thr
545                 550                 555                 560

Leu Ile Val Asn Ala Asp Glu Asp Ala Glu Val Lys Val Glu Gly Ser
                565                 570                 575

Val His Asn Lys Gly Trp Thr Leu Glu Pro Val Asp Tyr Lys Asp Thr
            580                 585                 590

Ser Val Pro Glu Glu Ile Arg Ile Arg Gly Phe Arg Ile Asn Lys Ile
        595                 600                 605

Glu Gln Glu Glu Arg Asn
    610
```

<210> SEQ ID NO 34
<211> LENGTH: 2169
<212> TYPE: DNA
<213> ORGANISM: Cucumis melo

<400> SEQUENCE: 34

| | | | | | |
|---|---|---|---|---|---|
| ggcacgaggc | tcaatcgcac | ccaacatggc | ttcctctctc | gattccgctg | cactcactct | 60 |
| ttctaacctt | tccatcaatg | gagatttcgc | ttcttctctt | cccaatttac | agaagaatct | 120 |
| ccaccttcta | tctcctcaac | aggttgaatt | ggcgaagatt | tgttggaat  | tggggcagag | 180 |
| tcatcttttt | gagcattggg | ccgagcctgg | cgttgatgat | aatgaaaaga | aggctttctt | 240 |
| cgaccaggtt | gctcggctta | attctagcta | tcctgggggg | ttggcctcct | atatcaagac | 300 |
| tgccagggga | ctcttagcag | attccaaaga | aggaagaac  | ccatttgatg | gcttcactcc | 360 |
| ctctgttcca | actggtgaag | ttttgacttt | tggcgatgat | agctttgtca | gctttgagga | 420 |
| ccgaggtgta | agggaagctc | gaaaggctgc | atttgttctt | gttgctggtg | ggcttgggga | 480 |
| gcggctagga | tataatggaa | ttaaggtggc | tcttccagca | gaaactacta | caggcacatg | 540 |
| tttcttacag | agttacattg | aatacgtttt | ggctcttcga | gaagccagca | atagactggc | 600 |
| aggtgaaagt | gaaacagaga | ttccttttgt | tataatgaca | tcagatgata | ctcatacacg | 660 |
| tacagtagag | ctgttggaat | cgaattccta | ttttggaatg | aaaccctcac | aagttaaact | 720 |
| tctaaaacag | gaaaaagttg | cttgtttgga | tgataatgag | gccaggcttg | ccgttgatcc | 780 |
| acataacaaa | tataggattc | agaccaagcc | tcatggccat | ggggatgtcc | atgcacttct | 840 |
| gtactctagt | ggccttctca | aaaattggca | caatgctggt | ttaagatggg | ttctcttttt | 900 |
| ccaagataca | aatgggcttc | tattcaaggc | aattccagct | tctttgggtg | ttagtgctac | 960 |
| aagagagtac | catgttaatt | ctctagctgt | tccacgcaaa | gcaaagaag  | ccattggtgg | 1020 |
| aattactcgt | cttactcata | ctgatgggag | gtctatggtt | atcaatgtgg | aatataatca | 1080 |
| gcttgatcca | ctgcttagag | caactggatt | tcccgatggt | gacgtcaata | atgagaccgg | 1140 |
| ctactctcct | tttccaggaa | atataaatca | actaatttta | gaacttggtt | cctatattga | 1200 |
| ggagctgagc | aaaacacaag | gtgctataaa | ggaatttgtc | aatcccaaat | ataaagatgc | 1260 |
| taccaagact | tcttttcaagt | cttcaacccg | attggaatgt | atgatgcaag | attatccaaa | 1320 |
| gacattacct | ccatcggctc | gggttggatt | tacggtgatg | gatacctggg | ttgcttatgc | 1380 |
| tccagtgaag | aacaaccctg | aagatgctgc | taaggtaccg | aagggaaacc | cttatcacag | 1440 |
| tgctacttcg | ggggaaatgg | ccatctaccg | tgcaaatagt | cttgttctca | gaaaggcagg | 1500 |
| agttaaagta | gccgatccag | ttgaacaggt | gttcaatggc | caagaggttg | aagtctggcc | 1560 |
| tcgcatcacg | tggaaaccga | aatggggttt | gacctttca  | gagataaaaa | gcaaaatcaa | 1620 |
| tggaaattgc | tccatttctc | cgcgttctac | cttggttatc | aaggggaaaa | acgtttatct | 1680 |
| taaagatctc | tccttggatg | gaactcttat | tgtgaatgca | gatgaagatg | ctgaggtaaa | 1740 |

```
agtagagggt tcagtacata acaagggctg gacactcgaa cccgttgatt ataaagatac    1800
ttcagtacca gaagaaataa ggattagagg gttcagaatc aacaaaatcg agcaggaaga    1860
aagaaactga gcctacaact ttagcctgaa ataccttgaa ggtgaagttg ttatattcat    1920
ggcctttatt ggaccagttt tgctgtgaa ataattcttt ttccttactt taggaaaagg     1980
aaatttgtaa cgattttggt tctataataa atatgtattt taacgtggcc tggaataatt    2040
tgattgagta ataaaaatat tttggagatg gagaatgaaa tttctttgat acttctcctc    2100
acctttattt gaaaaaaaaa aaaaaaaaaa aaaaaaaaaa aaaaaaaaaa aaaaaaaaaa    2160
aaaaaaaaa                                                            2169

<210> SEQ ID NO 35
<211> LENGTH: 476
<212> TYPE: PRT
<213> ORGANISM: Cucumis melo

<400> SEQUENCE: 35

Met Ala Ser Ala Ala Thr Leu Ser Pro Ala Asp Thr Glu Lys Leu Ser
1               5                   10                  15

Lys Leu Lys Ala Ser Val Ser Gly Leu Thr Gln Ile Ser Glu Asn Glu
            20                  25                  30

Lys Ser Gly Phe Ile Asn Leu Val Ser Arg Tyr Leu Ser Gly Glu Ala
        35                  40                  45

Gln His Val Glu Trp Ser Lys Ile Gln Thr Pro Thr Asp Glu Val Val
    50                  55                  60

Val Pro Tyr Asp Ser Leu Ala Pro Val Pro Asn Asp Pro Ala Glu Thr
65                  70                  75                  80

Lys Lys Leu Leu Asp Lys Leu Val Val Leu Lys Leu Asn Gly Gly Leu
                85                  90                  95

Gly Thr Thr Met Gly Cys Thr Gly Pro Lys Ser Val Ile Glu Val Arg
            100                 105                 110

Asn Gly Leu Thr Phe Leu Asp Leu Ile Val Ile Gln Ile Glu Asn Leu
        115                 120                 125

Asn Ser Lys Tyr Gly Cys Asn Val Pro Leu Leu Leu Met Asn Ser Phe
    130                 135                 140

Asn Thr His Asp Thr Gln Lys Ile Ile Glu Lys Tyr Lys Gly Ser
145                 150                 155                 160

Asn Val Asp Ile His Thr Phe Asn Gln Ser Gln Tyr Pro Arg Leu Val
                165                 170                 175

Ala Glu Asp Tyr Leu Pro Leu Pro Ser Lys Gly Arg Thr Asp Lys Asp
            180                 185                 190

Gly Trp Tyr Pro Pro Gly His Gly Asp Val Phe Pro Ser Leu Lys Asn
        195                 200                 205

Ser Gly Lys Leu Asp Ala Leu Ile Ala Gln Gly Lys Glu Tyr Val Phe
    210                 215                 220

Val Ala Asn Ser Asp Asn Leu Gly Ala Val Val Asp Leu Gln Ile Leu
225                 230                 235                 240

Asn His Leu Ile Gln Asn Lys Asn Glu Tyr Cys Met Glu Val Thr Pro
                245                 250                 255

Lys Thr Leu Ala Asp Val Lys Gly Gly Thr Leu Ile Ser Tyr Glu Gly
            260                 265                 270

Lys Val Gln Leu Leu Glu Ile Ala Gln Val Pro Asp Glu His Val Asn
        275                 280                 285

Glu Phe Lys Ser Ile Gln Lys Phe Lys Ile Phe Asn Thr Asn Asn Leu
```

```
                290                 295                 300
Trp Val Asn Leu Lys Ala Ile Lys Arg Leu Val Glu Ala Asn Ala Leu
305                 310                 315                 320

Lys Met Glu Ile Ile Pro Asn Pro Lys Glu Val Asp Gly Ile Lys Val
                325                 330                 335

Leu Gln Leu Glu Thr Ala Ala Gly Ala Ala Ile Arg Phe Phe Asp His
                340                 345                 350

Ala Ile Gly Ile Asn Val Pro Arg Ser Arg Phe Leu Pro Val Lys Ala
                355                 360                 365

Thr Ser Asp Leu Leu Val Gln Ser Asp Leu Tyr Thr Leu Val Asp
370                 375                 380

Gly Phe Val Leu Arg Asn Lys Ala Arg Lys Asp Pro Ser Asn Pro Ser
385                 390                 395                 400

Ile Glu Leu Gly Pro Glu Phe Lys Lys Val Gly Asn Phe Leu Ser Arg
                405                 410                 415

Phe Lys Ser Ile Pro Ser Ile Ile Glu Leu Asp Ser Leu Lys Val Val
                420                 425                 430

Gly Asp Val Ser Phe Gly Ala Gly Val Val Leu Lys Gly Lys Val Thr
                435                 440                 445

Ile Ser Ala Lys Pro Gly Thr Lys Leu Ala Val Pro Asp Asn Ala Val
                450                 455                 460

Ile Ala Asn Lys Glu Ile Asn Gly Pro Glu Asp Phe
465                 470                 475

<210> SEQ ID NO 36
<211> LENGTH: 1640
<212> TYPE: DNA
<213> ORGANISM: Cucumis melo

<400> SEQUENCE: 36
atggcatctg ctgctactct tagccctgct gatactgaga agctttccaa acttaaagct      60
tctgtttctg gacttaccca gattagtgag aatgagaaat ctggatttat caaccttgtc     120
tctcgctatc tcagtgggga agcacagcat gttgaatgga gcaagatcca gactccaaca     180
gatgaagtag tggttcctta tgattccttg gcacctgtac ctaatgatcc tgctgaaact     240
aagaaactat tggacaaact tgttgttttg aagcttaatg gaggtttggg gaccacaatg     300
ggctgcacag gtcctaagtc agtcattgaa gtccggaatg gtttgacatt tcttgacttg     360
attgttatcc aaatagagaa tcttaattcc aaatatgggt gcaacgttcc tttacttctg     420
atgaactcat ttaacactca tgatgatacc caaaagatca ttgaaaaata caaaggttca     480
aatgtggata ttcatacatt caaccagagc caatatccac gtttggttgc tgaggactat     540
cttccactcc ctagcaaagg acgcactgac aaggatggat ggtaccctcc tggacatggt     600
gatgttttcc catccttgaa aaacagcggc aaacttgatg ccctgatagc tcagggcaag     660
gaatatgtct ttgttgcaaa ctctgacaac ttaggtgccg ttgtggactt gcaaattta      720 aatcatttga tacagaacaa gaatgagtac tgcatggagg tgactcccaa accttggct     780 gatgtgaagg gtggtactct tatttcttat gaagggaagg ttcagttgct gaaattgct     840 caagtccctg atgaacacgt caatgaattc aagtcaattc agaaattcaa attttcaac    900 actaacaatt tgtgggtgaa cttgaaagca atcaaaggc ttgtggaagc aatgcactt     960 aagatggaga ttattccaaa tcccaaggaa gttgatggga ttaaagttct tcagctcgaa    1020
acagcagctg gtgcagcaat caggttcttt gatcatgcaa ttggtattaa tgtgccacga    1080
tcacgatttc ttcctgtcaa agcaacttca gatttgcttc ttgtccagtc tgatctctat    1140
```

```
actctagttg atggctttgt ccttcgcaac aaggctagaa aagatccttc caatccttct    1200
attgaattgg ggcccgaatt caagaaggtt ggtaacttcc tgagccgatt caagtcaatt    1260
ccgagcatca ttgaacttga tagccttaaa gtggttggcg atgtttcgtt cggggctggt    1320
gtcgttctca aggggaaagt gactatttcg gctaaaccag gacgaaatt ggctgtaccc     1380 gataacgccg taatagcaaa caaggaaatc aatggcccag aagatttcta aacaattggt    1440
tgcctttcac aactctttca gagcagaaac cttatggcat ctgcgtaccc tttctctttt    1500
aataccaaca aaatcgtgca gttttgtctg taatatgcgt ccagtttggg aactggtgtt    1560
tttgataaga tgaactttgt tggcattaaa acaaaatga gtttatatta atatataata     1620
cagaataagc aaaagttaag                                                 1640
```

<210> SEQ ID NO 37
<211> LENGTH: 344
<212> TYPE: PRT
<213> ORGANISM: Cucumis melo

<400> SEQUENCE: 37

```
Met Ala Ser Pro Val Glu Ser Arg Arg Pro Glu Leu Arg Lys Asp Ser
1               5                   10                  15

Val Thr Asn Arg Trp Val Ile Phe Ser Pro Ala Arg Ala Lys Arg Pro
            20                  25                  30

Ser Asp Phe Lys Ser Lys Ser Pro Ala Pro Ser Ser Thr Asp Ser Pro
        35                  40                  45

Gln Thr Cys Pro Phe Cys Ile Gly Gln Glu His His Cys Ala Pro Glu
    50                  55                  60

Ile Phe Arg Phe Pro Pro Gln Asn Pro Asp Trp Lys Val Arg Val Ile
65                  70                  75                  80

Gln Asn Leu Tyr Pro Ala Leu Ser Arg Asp Lys Asp Leu Asp Ser Ser
                85                  90                  95

Thr Ser Leu Ser Ser Gly Ser Leu Leu Trp Gly Cys Leu Leu Asp Gly
            100                 105                 110

Tyr Gly Phe His Asp Val Ile Ile Glu Ser Pro Val His Ser Val His
        115                 120                 125

Leu Ser Asp Leu Thr Pro Glu Asp Val Ala Gln Val Leu Phe Ala Tyr
    130                 135                 140

Lys Lys Arg Ile Leu Gln Leu Ala Ser Asp Ser Ile Lys Tyr Val
145                 150                 155                 160

Gln Val Phe Lys Asn His Gly Ala Ser Gly Ala Ser Met Thr His
                165                 170                 175

Pro His Ser Gln Met Val Gly Leu Pro Val Ile Pro Pro Ser Val Thr
            180                 185                 190

Thr Arg Leu Asp Ser Met Lys Gln Tyr Phe Asn Glu Thr Gly Lys Cys
        195                 200                 205

Ser Ile Cys His Val Pro Thr Lys Asp Leu Leu Val Asp Glu Ser Val
    210                 215                 220

His Phe Ile Ser Val Val Pro Tyr Ala Ala Ser Phe Pro Phe Glu Leu
225                 230                 235                 240

Trp Ile Val Pro Arg Asp His Val Ser His Phe His Glu Leu Asp Gln
                245                 250                 255

Glu Lys Ala Val Asp Leu Gly Gly Leu Leu Lys Val Thr Leu Ile Lys
            260                 265                 270

Met Ser Leu Gln Leu Asn Lys Pro Pro Phe Asn Phe Met Ile His Thr
        275                 280                 285
```

```
Ser Pro Leu Gln Ala Ser Asp Ser Asp Leu Ala Tyr Ser His Trp Phe
    290                 295                 300

Phe Gln Ile Val Pro His Leu Ser Gly Val Gly Gly Phe Glu Leu Gly
305                 310                 315                 320

Thr Gly Cys Tyr Ile Asn Pro Val Phe Pro Glu Asp Ala Ala Lys Val
                325                 330                 335

Met Arg Glu Val Asn Ile Ser Ile
            340

<210> SEQ ID NO 38
<211> LENGTH: 1500
<212> TYPE: DNA
<213> ORGANISM: Cucumis melo

<400> SEQUENCE: 38
ctaacaacgt tctaggctat ccggtcagaa tttctttcag cctttttcgc cgtggaaaat      60
ggcgtcgccg gttaatctc gccgtcccga actccggaag gactcagtaa ctaatcgttg     120
ggtcatattc tcacctgctc gagctaaacg accctccgat ttcaaatcca atccccagc     180 cccttcttca actgattctc ctcaaacatg ccccttctgc attggccaag agcaccactg     240
cgctcccgag atctttcgat ttcctcctca gaaccccgac tggaaagttc gcgttattca     300
aaatctctat cctgctctca gtagggataa ggatctcgat tcttcaactt ccctgagctc     360
cggttcactc ttatggggtt gccttttgga cgggtatggg ttccacgacg tcatcattga     420
gtctcctgtt cactcagttc atctctctga tttgaccccc gaggatgtcg ctcaagttct     480
ttttgcgtat aagaagcgga ttctgcagct cgcaagcgat gacagcatca aatatgttca     540
ggtgtttaaa aaccatggtg cctcagctgg ggcatcaatg acgcaccccc acagtcagat     600
ggtgggtctt ccagtcattc ctccctctgt tactactcga cttgatagta tgaagcagta     660
tttcaatgag acggggaaat gtagcatttg tcatgttcct acaaaggacc ttttggttga     720
tgaatcagtc catttcattt ctgttgttcc ctatgcagcc tcgtttccgt ttgagctctg     780
gatcgttccc cgtgaccatg tttctcattt tcatgagcta gaccaggaga aggctgttga     840
tcttggaggg ctattgaaag tgacactcat aaagatgtct ctgcagctga acaaaccacc     900
attcaacttc atgattcaca cttctcccct gcaggcttcg gattcagact agcttacag     960 ccactggttt tttcagattg ttcctcacct ttctggtgta gggggttttg aactaggaac    1020
tggttgctac atcaatcctg ttttttccaga ggatgctgct aaagtcatga gggaggttaa    1080
catttctata taggctcagg cccaggtacg ttttattctg atgaaaaatc tctccctttt    1140
ctttctggtg tgagattaga actggcctac ctttttcctt atgaataggt taacactagt    1200
tttttttttt tcctgtaaaa aatctgtcat aacttcactt gggatgtttc tgggaaatcg    1260
ttcgtgagta atggctactt gtttgttgat gattctccta tttggccctg aaagcgagat    1320
ctcttacttt gaaatctatt gtgcacagga tatatattac ctaggtagca caagtacaat    1380
aatgagatgg acgcaacatg acatggacat ggtaacacac tctttaacat atatcatttt    1440
tatacatttt gatgaaaact ggatattaat tttgattttg tttgaaaact ttgcaattaa    1500

<210> SEQ ID NO 39
<211> LENGTH: 14
<212> TYPE: PRT
<213> ORGANISM: Artificial sequence
<220> FEATURE:
<223> OTHER INFORMATION: A peptide sequence obtained from the peptide
      microsequencing of the purified melon UGGPase
```

-continued

```
<400> SEQUENCE: 39

Leu Asn Ser Ser Tyr Pro Gly Gly Leu Ala Ser Tyr Ile Lys
1               5                   10

<210> SEQ ID NO 40
<211> LENGTH: 14
<212> TYPE: PRT
<213> ORGANISM: Artificial sequence
<220> FEATURE:
<223> OTHER INFORMATION: A peptide sequence obtained from the peptide
      microsequencing of the purified melon UGGPase

<400> SEQUENCE: 40

Leu Thr Phe Gly Asp Asp Ser Phe Val Ser Phe Glu Asp Arg
1               5                   10

<210> SEQ ID NO 41
<211> LENGTH: 26
<212> TYPE: PRT
<213> ORGANISM: Artificial sequence
<220> FEATURE:
<223> OTHER INFORMATION: A peptide sequence obtained from the peptide
      microsequencing of the purified melon UGGPase

<400> SEQUENCE: 41

Trp Val Leu Phe Phe Gln Asp Thr Asn Gly Leu Leu Phe Lys Ala Ile
1               5                   10                  15

Pro Ala Ser Leu Gly Val Ser Ala Thr Arg
            20                  25

<210> SEQ ID NO 42
<211> LENGTH: 23
<212> TYPE: PRT
<213> ORGANISM: Artificial sequence
<220> FEATURE:
<223> OTHER INFORMATION: A peptide sequence obtained from the peptide
      microsequencing of the purified melon UGGPase

<400> SEQUENCE: 42

Ser Pro Phe Pro Gly Asn Ile Asn Gln Leu Ile Leu Glu Leu Gly Ser
1               5                   10                  15

Tyr Ile Glu Glu Leu Ser Lys
            20

<210> SEQ ID NO 43
<211> LENGTH: 9
<212> TYPE: PRT
<213> ORGANISM: Artificial sequence
<220> FEATURE:
<223> OTHER INFORMATION: A peptide sequence obtained from the peptide
      microsequencing of the purified melon UGGPase

<400> SEQUENCE: 43

Lys Val Ala Asp Pro Val Glu Gln Val
1               5

<210> SEQ ID NO 44
<211> LENGTH: 7
<212> TYPE: PRT
<213> ORGANISM: Artificial sequence
<220> FEATURE:
<223> OTHER INFORMATION: A peptide sequence obtained from the peptide
      microsequencing of the purified melon UGGPase

<400> SEQUENCE: 44

Glu Val Glu Val Trp Pro Arg
1               5
```

<210> SEQ ID NO 45
<211> LENGTH: 9
<212> TYPE: PRT
<213> ORGANISM: Artificial sequence
<220> FEATURE:
<223> OTHER INFORMATION: A peptide sequence obtained from the peptide microsequencing of the purified melon UGGPase

<400> SEQUENCE: 45

Trp Gly Leu Thr Phe Ser Glu Ile Lys
1               5

<210> SEQ ID NO 46
<211> LENGTH: 877
<212> TYPE: DNA
<213> ORGANISM: Artificial sequence
<220> FEATURE:
<223> OTHER INFORMATION: Cauliflower mosaic virus 35S promoter

<400> SEQUENCE: 46

```
aagcttgcat gcctgcaggt ccccagatta gccttttcaa tttcagaaag aatgctaacc      60
cacagatggt tagagaggct tacgcagcag gtctcatcaa gacgatctac ccgagcaata     120
atctccagga aatcaaatac cttcccaaga aggttaaaga tgcagtcaaa agattcagga     180
ctaactgcat caagaacaca gagaaagata tatttctcaa gatcagaagt actattccag     240
tatggacgat tcaaggcttg cttcacaaac caaggcaagt aatagagatt ggagtctcta     300
aaaaggtagt tcccactgaa tcaaaggcca tggagtcaaa gattcaaata gaggacctaa     360
cagaactcgc cgtaaagact ggcgaacagt tcatacagag tctcttacga ctcaatgaca     420
agaagaaaat cttcgtcaac atggtggagc acgacacact tgtctactcc aaaaatatca     480
agatacagt ctcagaagac caaagggcaa ttgagacttt tcaacaaagg gtaatatccg     540
gaaacctcct cggattccat tgcccagcta tctgtcactt tattgtgaag atagtggaaa     600
aggaaggtgg ctcctacaaa tgccatcatt gcgataaagg aaaggccatc gttgaagatg     660
cctctgccga cagtggtccc aaagatggac ccccacccac gaggagcatc gtggaaaaag     720
aagacgttcc aaccacgtct tcaaagcaag tggattgatg tgatatctcc actgacgtaa     780
gggatgacgc acaatcccac tatccttcgc aagacccttc ctctatataa ggaagttcat     840
ttcatttgga gagaacacgg gggactctag aggatcc                              877
```

<210> SEQ ID NO 47
<211> LENGTH: 2322
<212> TYPE: DNA
<213> ORGANISM: Artificial sequence
<220> FEATURE:
<223> OTHER INFORMATION: Arabidopsis At6669 promoter

<400> SEQUENCE: 47

```
aagctttaag ctccaagccc acatctatgc acttcaacat atcttttct agatgagttg      60
gtaaaagtag aaaagatat gatgatttta aatttgtttc tatttatatg tgttcatcga     120
aacttcattt ttttagttt taatagagag tttatgac ttaaaaat tgatttaaa          180
ctgtgtcaaa aattaaaagg acaataaaaa atttgcatac aaccgaaaat acttatattt     240
agacaagaaa aaataatact tgtgatgctg attttatttt attatatatc atgaatcatg     300
atcatccaat tttccggata agccaaagtc aaaatgatgg gttcccccta atctttattg     360
ctgagaaata gatgtatatt cttagatagt aatataaaat tgggttaaag aatgatgatt     420
cgattatagc ctcaactaga agatacgtgt agtgcaggtg tgtagttaac tggtggtagt     480
```

```
ggcagacaac cagattagga gttaaataaa gcctttagat ttgagagatt gaaatattcg      540
attggaacct ttctagattt ttacagccat ctaaaattag atgcagatca cctactacca      600
ttcaaaaatg aacaaaataa tttcatttac attttcctag cataagatat aataataaaa      660
tagtgctcat tttaattact ttttctaaat attttcgtta ttttaaattt tgcttgtcta      720
tactctacag ctcatttaat aacggaaaca aaaataattg cagggatacg gatgggtagc      780
tttcaaaact tacatcatct tctgtttctt gagatcaact attttggag ctttgtctca       840 atcgtaccaa aggataatgg tcctacctcc ttttgcattc ttaactttat cttctctact      900
tatttctttt ttgggatttt tgggggtatt attttatctt ttgtagatat acacattgat      960
ttactacaaa cgtatactac tatccatctt caactcttcg gaatatgatt tcgaaaaaac     1020
tatgaagatt aacgggtatc ttaaacatgt taagatacac cggacaattt tcatttagaa     1080
gaattgatat gcaattaaca ataaatagtt gatgatcttt tagttttgaa gatgtgcgtt     1140
aagacttaag cgtgtggtaa caaggtggga ctcgggcaac gcaaagcctt gtagagtcca     1200
cttgctcaac ttgtctttct tttatctctt ttccaagtct caagattcaa tgaactccgt     1260
gtaacacaaa cacgcccata gatgagctca tttttggtat ttccaatatt gccactccat     1320
gataatatca tctagggatg gggttcattt attttgaaat ctcaacaaat ctcgtcgatt     1380
ctaacacaca tgattgattt gtttacttac ttgaaagttg gcaactatct gggattaaaa     1440
tttatctttt tctactgcta gctagaagca tctatatatg ttagcctaat acgtggaaga     1500
tgtcattgct aataatggct aaagatgtgt attaattttt cttctttttt ccttgaatt      1560 ttgttctttg acataaacta tgctgtcaaa atgtgtagaa tcttttaca taaatcattc      1620 cctgttacac actaaaaggt tcacaacgga cgattgtatt ggacttccag atcataaacc     1680
atgcaaaact gaaaaccaca agaataatta gttctaactt tagaacgttc gtacgtgttt     1740
catgttcaaa aagcgtcaat tataaaagtt gggaaattac ttttgagttt tgacatttct     1800
aaggacagtc aaatatgaca acattgggat gcaacttacc ttgtattaac ttattttgtt     1860
ataaaaccat atattacata ttttaaaggg ttgataaata atcaaatata ccaaaacata     1920
gcttttcaat atatttgtaa aacacgtttg gtctactagc taattatgag aacatttgtt     1980
caatgcatga ttatctagta tctactagtg gattatgaaa attagatatt ttcattgcat     2040
gattatcttc catatatagt gataacatca aaagaatcta caccaattat tgcattttt      2100 cattatataa taagcactaa actgtaaaat tatattcagc cacccaaacc atgcaaaatc     2160
accttaaagg cttaaacaca taacagccat tacgagtcac aggtaagggt ataatagtaa     2220
agaatcaatc tatataatat acgacccacc ctttctcatt cttctggag agtaacatcg      2280 agacaaagaa gaaaaactaa aaaagagaac cccaaaggat cc                        2322
```

<210> SEQ ID NO 48
<211> LENGTH: 976
<212> TYPE: DNA
<213> ORGANISM: Artificial sequence
<220> FEATURE:
<223> OTHER INFORMATION: Maize ubiquitin gene derived promoter

<400> SEQUENCE: 48

```
gtgcagcgtg acccggtcgt gcccctctct agagataatg agcattgcat gtctaagtta       60
taaaaaatta ccacatattt ttttgtcac acttgtttga agtgcagttt atctatcttt      120
atacatatat ttaaacttta ctctacgaat aatataatct atagtactac aataatatca     180
gtgttttaga gaatcatata aatgaacagt tagacatggt ctaaaggaca attgagtatt     240
```

```
ttgacaacag gactctacag ttttatctttt ttagtgtgca tgtgttctcc ttttttttg      300 caaatagctt cacctatata atacttcatc cattttatta gtacatccat ttagggttta      360
gggttaatgg ttttttataga ctaattttttt tagtacatct atttttattct attttagcct   420 ctaaattaag aaaactaaaa ctctatttta gttttttttat ttaataattt agatataaaa     480
tagaataaaa taaagtgact aaaaattaaa caaatacccct ttaagaaatt aaaaaaacta     540
aggaaacatt tttcttgttt cgagtagata atgccagcct gttaaacgcc gtcgacgagt     600
ctaacggaca ccaaccagcg aaccagcagc gtcgcgtcgg gccaagcgaa gcagacggca    660
cggcatctct gtcgctgcct ctggaccccct ctcgagagtt ccgctccacc gttggacttg     720
ctccgctgtc ggcatccaga aattgcgtgg cggagcggca gacgtgagcc ggcacggcag     780
gcggcctcct cctcctctca cggcacggca gctacggggg attcctttcc caccgctcct    840
tcgctttccc ttcctcgccc gccgtaataa atagacaccc cctccacacc ctctttcccc     900
aacctcgtgt tgttcggagc gcacacacac acaaccagat ctcccccaaa tccacccgtc     960
ggcacctccg cttcaa                                                       976
```

<210> SEQ ID NO 49
<211> LENGTH: 913
<212> TYPE: DNA
<213> ORGANISM: Artificial sequence
<220> FEATURE:
<223> OTHER INFORMATION: Rice actin gene derived promoter

<400> SEQUENCE: 49

```
tcgaggtcat tcatatgctt gagaagagag tcgggatagt ccaaaataaa acaaaggtaa     60
gattacctgg tcaaaagtga aaacatcagt taaaaggtgg tataaagtaa aatatcggta    120
ataaaaggtg gcccaaagtg aaatttactc ttttctacta ttataaaaat tgaggatgtt    180
ttgtcggtac tttgatacgt catttttgta tgaattggtt tttaagttta ttcgcgattt    240
ggaaatgcat atctgtattt gagtcggttt ttaagttcgt tgcttttgta aatacagagg    300
gatttgtata agaaatatct ttaaaaaacc catatgctaa tttgacataa tttttgagaa    360
aaatatatat tcaggcgaat tccacaatga acaataataa gattaaaata gcttgccccc    420
gttgcagcga tgggtatttt ttctagtaaa ataaaagata aacttagact caaaacattt    480
acaaaaacaa cccctaaagt cctaaagccc aaagtgctat gcacgatcca tagcaagccc    540
agcccaaccc aacccaaccc aacccacccc agtgcagcca actggcaaat agtctccacc    600
cccggcacta tcaccgtgag ttgtccgcac caccgcacgt ctcgcagcca aaaaaaaaa    660 aagaaagaaa aaaagaaaa agaaaaacag caggtgggtc cgggtcgtgg gggccggaaa    720
agcgaggagg atcgcgagca gcgacgaggc ccggcccctcc ctccgcttcc aaagaaacgc    780
cccccatcgc cactatatac ataccccccc ctctcctccc atccccccaa ccctaccacc    840
accaccacca ccacctcctc ccccctcgct gccggacgac gagctcctcc ccctccccc    900 tccgccgccg ccg                                                         913
```

<210> SEQ ID NO 50
<211> LENGTH: 1172
<212> TYPE: DNA
<213> ORGANISM: Artificial sequence
<220> FEATURE:
<223> OTHER INFORMATION: Synthetic Super MAS promoter

<400> SEQUENCE: 50

```
tacaggccaa attcgctctt agccgtacaa tattactcac cggtgcgatg cccccccatcg     60
```

```
taggtgaagg tggaaattaa tgatccatct tgagaccaca ggcccacaac agctaccagt    120
ttcctcaagg gtccaccaaa aacgtaagcg cttacgtaca tggtcgataa gaaaaggcaa    180
tttgtagatg ttaacatcca acgtcgcttt cagggatccc gaattccaag cttggaattc    240
gggatcctac aggccaaatt cgctcttagc cgtacaatat tactcaccgg tgcgatgccc    300
cccatcgtag gtgaaggtgg aaattaatga tccatcttga gaccacaggc ccacaacagc    360
taccagtttc ctcaagggtc caccaaaaac gtaagcgctt acgtacatgg tcgataagaa    420
aaggcaattt gtagatgtta acatccaacg tcgctttcag ggatcccgaa ttccaagctt    480
ggaattcggg atcctacagg ccaaattcgc tcttagccgt acaatattac tcaccggtgc    540
gatcccccca tcgtaggtga aggtggaaat taatgatcca tcttgagacc acaggcccac    600
aacagctacc agtttcctca agggtccacc aaaaacgtaa gcgcttacgt acatggtcga    660
taagaaaagg caatttgtag atgttaacat ccaacgtcgc tttcagggat cccgaattcc    720
aagcttgggc tgcaggtcaa tcccattgct tttgaagcag ctcaacattg atctctttct    780
cgagggagat ttttcaaatc agtgcgcaag acgtgacgta agtatccgag tcagttttta    840
tttttctact aatttggtcg tttatttcgg cgtgtaggac atggcaaccg ggcctgaatt    900
tcgcgggtat tctgtttcta ttccaacttt ttcttgatcc gcagccatta acgacttttg    960
aatagatacg ctgacacgcc aagcctcgct agtcaaaagt gtaccaaaca acgctttaca    1020
gcaagaacgg aatgcgcgtg acgctcgcgg tgacgccatt tcgccttttc agaaatggat    1080
aaatagcctt gcttcctatt atatcttccc aaattaccaa tacattacac tagcatctga    1140
atttcataac caatctcgat acaccaaatc ga                                  1172
```